US012698397B2

(12) United States Patent
Kendrick et al.

(10) Patent No.: US 12,698,397 B2
(45) Date of Patent: Aug. 4, 2026

(54) COLOUR-STABLE PREPARATION OF A MAGNESIUM CHLOROPHYLLIN ALKALI METAL SALT OR ALKALI EARTH METAL SALT FROM NATURAL SOURCES OF CHLOROPHYLL

(71) Applicant: Givaudan SA, Vernier (CH)

(72) Inventors: Andrew Kendrick, Hatton (GB); Stuart David Thorpe, Birmingham (GB)

(73) Assignee: Givaudan SA, Vernier (CH)

( * ) Notice: Subject to any disclaimer, the term of this patent is extended or adjusted under 35 U.S.C. 154(b) by 0 days.

(21) Appl. No.: 18/423,614

(22) Filed: Jan. 26, 2024

(65) Prior Publication Data

US 2024/0166882 A1 May 23, 2024

Related U.S. Application Data

(62) Division of application No. 16/031,222, filed on Jul. 10, 2018, now Pat. No. 11,912,875.

(60) Provisional application No. 62/531,081, filed on Jul. 11, 2017.

(51) Int. Cl.

| | |
|---|---|
| ***C09B 61/00*** | (2006.01) |
| ***A23L 2/58*** | (2006.01) |
| ***A23L 5/43*** | (2016.01) |
| ***C07D 487/22*** | (2006.01) |
| ***C09B 67/20*** | (2006.01) |
| ***C09B 67/42*** | (2006.01) |
| ***C09B 67/54*** | (2006.01) |
| ***C12C 5/04*** | (2006.01) |

(52) U.S. Cl.

CPC ................ *C09B 61/00* (2013.01); *A23L 2/58* (2013.01); *A23L 5/43* (2016.08); *C07D 487/22* (2013.01); *C09B 67/006* (2013.01); *C09B 67/0092* (2013.01); *C09B 67/0096* (2013.01); *C12C 5/04* (2013.01); *C12G 2200/21* (2013.01)

(58) Field of Classification Search

None

See application file for complete search history.

(56) References Cited

U.S. PATENT DOCUMENTS

| | | | |
|---|---|---|---|
| 2,428,740 | A | 10/1947 | Thomas |
| 2,713,584 | A | 7/1955 | Gisvold |
| 3,274,073 | A | 9/1966 | Burdick |
| 2017/0174889 | A1 | 6/2017 | Shalev et al. |

FOREIGN PATENT DOCUMENTS

| | | | |
|---|---|---|---|
| CA | 432007 | A | 12/1945 |
| GB | 625727 | A | 7/1949 |

OTHER PUBLICATIONS

Lopez-Carballo, G., Hernández-Muñoz, P., Gavara, R., & Ocio, M. J. (2008). Photoactivated chlorophyllin-based gelatin films and coatings to prevent microbial contamination of food products. International journal of food microbiology, 126(1-2), 65-70. (Year: 2008).*

Bartos, Stephen A., et al., "Teachers' knowledge structures for nature of science and scientific inquiry: Conceptions and classroom practice", Journal of Research in Science Teaching, dated Nov. 1, 2014, pp. 1150-1184, Abstract only.

International Preliminary Report on Patentability for PCT Application No. PCT/US2018/041407, dated Jan. 14, 2020.

Han, J., Wang, Y., Ma, J., Wu, Y., Hu, Y., Ni, L., & Li, Y., "Simultaneous aqueous two-phase extraction and saponification reaction of chlorophyll from silkworm excrement", dated Aug. 2013, Separation and Purification Technology, 115, pp. 51-56.

Brune, D. C., & San Pietro, A., "Some newly observed correlations between structure and photochemical activity in chlorophyll in a and several derivatives", dated 1974, Archives of biochemistry and biophysics, 163(2), pp. 552-560.

US Department of Agriculture, Wall, Monroe E., "Preparation of Chlorophyll Derivatives for Industrial and Pharmaceutical Use", dated Mar. 1951, AIC-299, 12 pages.

* cited by examiner

*Primary Examiner* — Dale R Miller

(74) *Attorney, Agent, or Firm* — Curatolo Sidoti & Trillis Co., LPA; Salvatore A. Sidoti; Trillis Trillis, III

(57) ABSTRACT

The present invention provides a method for preparing a colour-stable preparation of a magnesium chlorophyllin alkali metal salt or alkali earth metal salt from natural sources of chlorophyll. The invention further provides a colour-stable and substantially pure pigment composition comprising a vibrant green magnesium chlorophyllin in the form of an alkali metal or alkali earth metal salt, e.g. those prepared by the methods of the invention, and the use of the salts and compositions of the invention as colouring agents, in particular as food colouring agents, and as medicaments and disinfectants.

27 Claims, No Drawings

COLOUR-STABLE PREPARATION OF A MAGNESIUM CHLOROPHYLLIN ALKALI METAL SALT OR ALKALI EARTH METAL SALT FROM NATURAL SOURCES OF CHLOROPHYLL

REFERENCE TO RELATED APPLICATIONS

The present application is a divisional of U.S. Ser. No. 16/031,222, filed Jul. 10, 2018, which claims the benefit of the filing date of United States Provisional Application For Patent Ser. No. 62/531,081, filed Jul. 11, 2017, both of which applications are hereby incorporated by reference in their entireties.

FIELD OF THE INVENTION

The present invention relates to a method for preparing a preparation of substantially pure, colour-stable magnesium chlorophyllin from natural sources of chlorophyll. More specifically, the magnesium chlorophyllin so prepared is in the form of an alkali metal or alkali earth metal salt which retains the vibrant green colour of magnesium chlorophyll. Hitherto it has not been possible to prepare magnesium chlorophyllin in any form to a sufficiently high degree of purity and with sufficient colour-stability to be industrially useful and forms of copper chlorophyllin are typically used instead. The invention therefore further relates to a colour-stable and substantially pure composition of a vibrant green magnesium chlorophyllin in the form of an alkali metal or alkali earth metal salt.

BACKGROUND OF THE INVENTION

Chlorophyllin is used as a colouring agent, as a medicament to treat certain aliments and in the photosensitisation-based combat of the microbial contamination of surfaces. The invention therefore further relates to use of the salts and compositions of the invention as colouring agents, in particular as food colouring agents, and as medicaments.

Chlorophyll is a green pigment ubiquitous in nature where it is found in the chloroplasts of plants and algae and cyanobacteria. It is an essential part of photosynthesis, the process in which these organisms convert light into chemical energy.

Chlorophyll is found in nature in a variety of forms. Common to all forms is the magnesium coordinating chlorin or porphyrin ring, although the exact side groups vary. All natural chlorophylls except chlorophyll c have a phytyl chain rendering such chlorophylls oil soluble rather than water soluble. The structure of chlorophyll a is recited below by way of example.

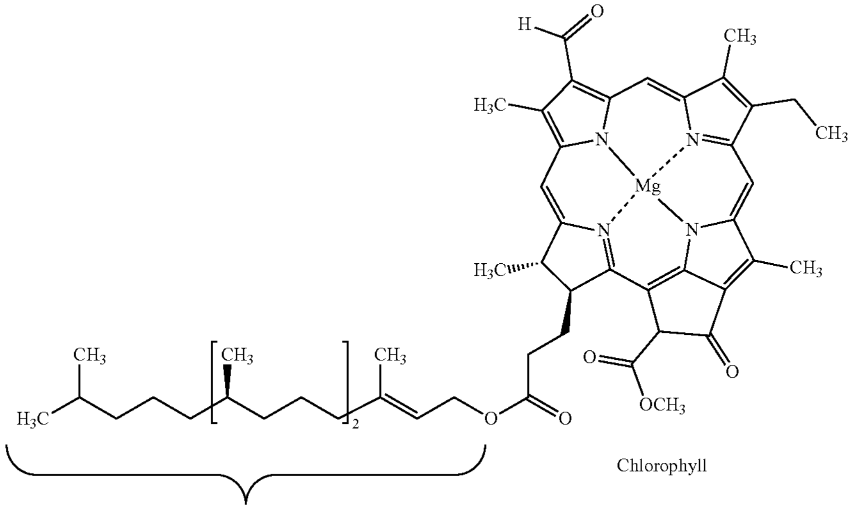

Chlorophyll phytyl side chain

In order to increase the water solubility of the phytyl group containing chlorophylls, the phytyl side chain may be removed, e.g. by hydrolysis, thus forming chlorophyllin. Depending on the degree of hydrolysis, the cyclopentenyl ring may also be cleaved, forming a third carboxy functional group (as shown below for chlorophyll a). The carboxy groups of chlorophyllin may be occupied with cations, e.g. cations of the alkali or alkali earth metals, to further increase water solubility.

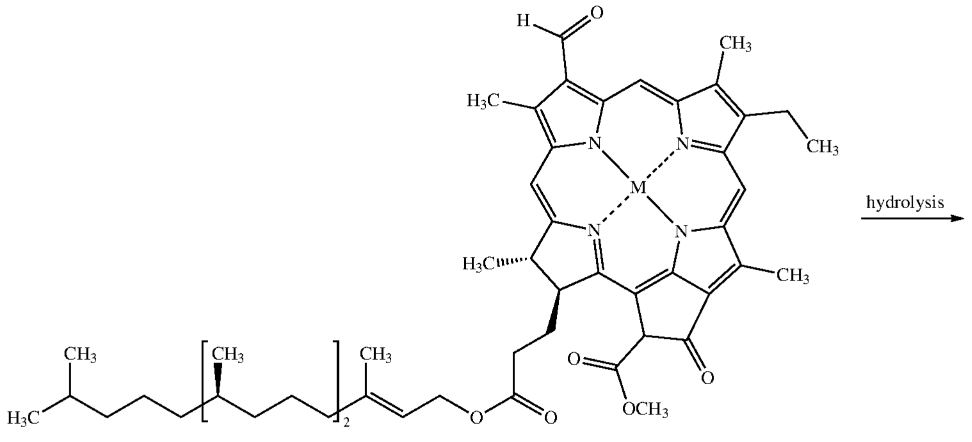

Chlorophyll a

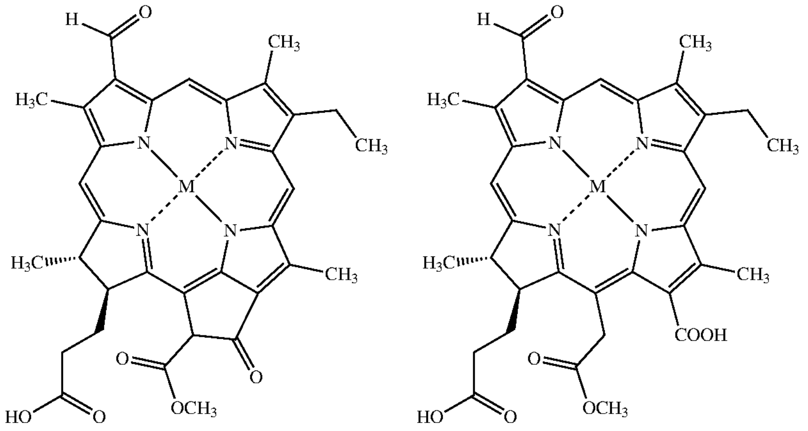

Chlorophyllins

Chlorophyllin has a number of industrial applications. Primarily it finds use as a colouring agent, in particular a food colouring additive, but it is also used therapeutically, in particular as an internal and external odour reducing agent, an antimicrobial, a chronic wound healing agent and in the treatment and prevention of cancer, and in the photosensitisation-based combat of the microbial contamination of surfaces.

In the EU food industry E140ii (Natural Green) describes the sodium and potassium salts of chlorophyllin a and b. According to EU 231/2012 to meet the criteria of E140ii, the content of total chlorophyllins must not be less than 95% of the sample dried at ca. 100° C. for 1 hour and wherein for a 100% sample:

$$E^{1\%}_{1\,cm}$$

700 at ca. 405 nm in aqueous solution at pH 9

$$E^{1\%}_{1\,cm}$$

140 at ca. 653 nm in aqueous solution at pH 9

In practice however, the metal complex of magnesium chlorophyllin is easily broken using simple acids and this changes the colour of the molecule dramatically (to a dull green or brown). Copper complexes of chlorophyllin are more resistant to such effects and inherently have a more vibrant green colour and so are used instead of magnesium chlorophyllin. However, copper chlorophyllin does not appear in nature and so may be perceived by consumers as an unnatural colour. Moreover, the current methods for producing magnesium chlorophyllin are unreliable and fail to produce a preparation of sufficient purity to meet typical standards for food additives or a preparation which has the desired green colour of chlorophyll and/or sufficient stability to be commercially viable.

To address these practical problems, at least in part, the inventors have developed a reproducible method for preparing alkali metal or alkali earth metal salts of magnesium chlorophyllin from natural sources of chlorophyll, wherein said salts have the desired green colour, are substantially colour stable and are sufficiently pure to meet stringent requirements for use as a food additive or as a medicament or an agent in the photosensitisation-based combat of the microbial contamination of surfaces.

SUMMARY OF THE INVENTION

Thus, in a first aspect the invention provides a method for preparing a colour-stable preparation of a magnesium chlorophyllin alkali metal salt or alkali earth metal salt, said method comprising either:

(a)(i) providing a liquid composition comprising a plant, cyanobacterial and/or algal extract containing a water-insoluble magnesium chlorophyll, wherein said extract has been prepared by treating plant, cyanobacterial and/or algal matter containing a water-insoluble magnesium chlorophyll with an organic solvent in which said chlorophyll is substantially soluble and chlorophyllin is substantially insoluble, wherein said composition has a oleoresin solids content of about 1% w/w to about 50% w/w and does not comprise an organic solvent in which chlorophyllin is substantially soluble; or (a)(ii) providing a liquid composition comprising a plant, cyanobacterial and/or algal extract containing a water-soluble magnesium chlorophyll, wherein said extract has been prepared by treating plant, cyanobacterial and/or algal matter containing a water-soluble magnesium chlorophyll with a substantially aqueous liquid in which said chlorophyll is substantially soluble, wherein said composition does not comprise an organic solvent in which chlorophyllin is substantially soluble; or (a)(iii) providing a liquid composition comprising the liquid component of plant, cyanobacterial and/or algal matter containing a water-insoluble magnesium chlorophyll, and an organic solvent in which said chlorophyll is substantially soluble and chlorophyllin is substantially insoluble, wherein said composition does not comprise an organic solvent in which chlorophyllin is substantially soluble; and either (b)(i) combining an amount of a basic inorganic alkali metal salt and/or a basic inorganic alkali earth metal salt, and optionally an amount of water, with an amount of said the liquid composition of step (a)(i), step (a)(ii) or step (a)(iii) and agitating the mixture so formed, wherein the amount of salt, and the amount of water if used, is sufficient to maintain a pH of equal to or greater than about 7.0 in the mixture; or (b)(ii) combining an amount of a non-nucleophilic organic base, ammonia, or a quaternary ammonium salt, and optionally, an alkali metal salt and/or an alkali earth metal salt, and optionally an amount of water, with an amount of said the liquid composition of step (a)(i), step (a)(ii) or step (a)(iii) and agitating the mixture so formed, wherein the amount of base, and the amount of water and salt, if used, is sufficient to maintain a pH of equal to or greater than about 7.0 in the mixture; or (b)(iii) combining an amount of said the liquid composition of step (a)(i), step (a)(ii) or step (a)(iii) with a chlorophyllase and alkali metal salt and/or an alkali earth metal salt, and optionally an amount of water, wherein the mixture so formed has a pH of equal to or greater than about 7.0; and (c) incubating the mixture of step (b)(i), (b)(ii) or (b)(iii) under conditions sufficient to convert magnesium chlorophyll to a magnesium chlorophyllin alkali metal salt or alkali earth metal salt; and either (d)(i) separating at least a portion of any aqueous phase of the mixture of step (c) from any water immiscible organic phase of the mixture of step (c); or (d)(ii) separating at least a portion of any precipitated magnesium chlorophyllin in the mixture of step (c) from any organic phase and redissolving said precipitate in an substantially aqueous liquid to form an aqueous phase; and (e) combining (i) an amount of a water immiscible aliphatic glycerol ester with an amount of the aqueous phase obtained in step (d)(i) and/or (d)(ii) and, optionally, (ii) an amount of a water immiscible organic solvent in which chlorophyll is substantially soluble and chlorophyllin is substantially insoluble, and agitating the mixture so formed, wherein the amount of ester added, and the amount of solvent if added, are sufficient to be capable of forming a water immiscible organic phase which may be separable from the aqueous phase and, if necessary, reduce the pH of the mixture so formed to about 7.0 to about 11.5; and (f) incubating the mixture under conditions sufficient to reduce the pH of the mixture so formed to about 7.0 to about 11.5, if necessary, and/or to partition substantially water insoluble components into the water immiscible organic phase; and (g) separating at least a portion of the aqueous phase of the mixture of step (f) from the water immiscible organic phase of the mixture of step (f); and (h) adding an amount of a water miscible organic solvent in which chlorophyllin is substantially soluble to an amount of the portion of the aqueous phase obtained in step (g) and agitating the mixture so formed, wherein the amount of organic solvent is sufficient to substantially solubilise chlorophyllin in the aqueous phase of the mixture;

(i) incubating the mixture of step (h) under conditions sufficient to substantially solubilise chlorophyllin in the aqueous phase of the mixture of step (h);

(j) separating at least a portion of any solids in the mixture of step (i) from the aqueous phase of said mixture, thereby providing an aqueous solution of said magnesium chlorophyllin alkali metal salt or alkali earth metal salt; and optionally, (k) removing at least a portion of said water miscible organic solvent from the aqueous chlorophyllin solution of step (j); and/or optionally, (l) removing at least a portion of the water present in the aqueous chlorophyllin solution of step (j) or step (k).

The final step of the above defined method provides a colour-stable preparation of a magnesium chlorophyllin alkali metal salt or alkali earth metal salt.

In another embodiment the invention provides a colour-stable preparation of a magnesium chlorophyllin alkali metal salt or alkali earth metal salt obtained or obtainable by the methods of the invention.

In another embodiment the invention provides a food, beverage, animal feed, pharmaceutical or cosmetic comprising the preparation or pigment composition of the invention as a colouring agent in an amount sufficient to impart a green colour to the composition or part thereof.

In another embodiment the invention provides a method for reducing odour in or on a subject, said method comprising administering a preparation or pigment composition of the invention or a pharmaceutical composition as described herein internally or externally to a subject in need thereof.

In another embodiment the invention provides A method for treating or preventing a microbial infection in or on a subject or a method promoting the healing of a chronic wound said method comprising administering a preparation or pigment composition of the invention to a chronic wound in or on a subject in need thereof.

In another embodiment the invention provides a method for treating or preventing cancer, said method comprising administering a preparation or pigment composition of the invention as a pharmaceutical composition to a subject in need thereof.

In another embodiment the invention provides a photosensitisation-mediated method for combating microbial contamination of surfaces, said method comprising administering a preparation or pigment composition of the invention to a surface and/or a microbe in association with said surface and irradiating said surface and/or microbe with light.

In another embodiment the invention provides a method for colouring a composition, said method comprising incorporating a preparation or pigment composition as claimed of the invention into the composition in an amount sufficient to impart colour to the composition.

In an additional embodiment the invention provides a pharmaceutical composition comprising a therapeutically effective amount of a preparation or pigment composition of the invention together with at least one pharmaceutically acceptable carrier, diluent or excipient.

In another embodiment the invention provides a chlorophyllin preparation or a pigment composition of the invention for use in therapy.

In an alternate embodiment the invention provides a method for reducing odour in or on a subject, said method comprising administering a preparation, pigment or pharmaceutical composition of the invention internally or externally to a subject in need thereof and optionally illuminating the subject or a part thereof with light.

In another embodiment the invention provides a method for treating or preventing a microbial infection in or on a subject, said method comprising administering a preparation, pigment or pharmaceutical composition of the invention to a subject in need thereof and optionally illuminating the subject or a part thereof with light.

In one aspect the invention provides a method for promoting the healing of a chronic wound, said method comprising administering a preparation, pigment or pharmaceutical composition of the invention to a chronic wound in or on a subject in need thereof and optionally illuminating the subject or a part thereof with light.

In another embodiment the invention provides a method for treating or preventing cancer, said method comprising administering a preparation, pigment or pharmaceutical composition of the invention to a subject in need thereof.

In another aspect the invention provides a photosensitisation-mediated method for combating microbial contamination of surfaces, said method comprising administering a preparation or pigment composition of the invention to a surface and/or a microbe in association with said surface and irradiating said surface and/or microbe with light. Optionally the method will relate to surfaces selected from industrial surfaces, surfaces in clinical, agricultural and food supply chain contexts, domestic surfaces, the surfaces of plants, crops, cropped produce, animal carcasses and livestock. Further the method may employ the application of the preparation or pigment composition of the invention in combination with a film forming agent capable of enhancing the retention of the chlorophyllin at the surface.

In an alternate embodiment the invention provides a photosensitisation-mediated surface disinfectant composition comprising a preparation or pigment composition of the invention and optionally one or more excipients or diluents. Optionally the disinfectant composition may further comprise one or more film forming agents capable of enhancing the retention of the chlorophyllin at the surface. In a specific embodiment of the method the film forming agent is selected from the group consisting of chitosan, alginate, pectin, cellulose, collagen, carrageen, gum arabic, gum karaya, starch and agar.

DETAILED DESCRIPTION OF THE INVENTION

Unless otherwise specified all references cited herein are incorporated by reference in their entirety.

The following definitions may be used for the interpretation of the claims and specification:

As used herein, the terms "comprises," "comprising," "includes," "including," "has," "having," "contains" or "containing," or any other variation thereof, are intended to cover a non exclusive inclusion. For example, a composition, a mixture, process, method, article, or apparatus that comprises a list of elements is not necessarily limited to only those elements but may include other elements not expressly listed or inherent to such composition, mixture, process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

Also, the indefinite articles "a" and "an" preceding an element or component of the invention are intended to be nonrestrictive regarding the number of instances (i.e. occurrences) of the element or component. Therefore "a" or "an" should be read to include one or at least one, and the singular word form of the element or component also includes the plural unless the number is obviously meant to be singular.

The term "invention" or "present invention" as used herein is a non-limiting term and is not intended to refer to any single embodiment of the particular invention but encompasses all possible embodiments as described in the specification and the claims. As used herein, the term "about" modifying the quantity of an ingredient or reactant of the invention employed refers to variation in the numerical quantity that can occur, for example, through typical measuring and liquid handling procedures used for making concentrates or use solutions in the real world; through inadvertent error in these procedures; through differences in the manufacture, source, or purity of the ingredients employed to make the compositions or carry out the methods; and the like. The term "about" also encompasses amounts that differ due to different equilibrium conditions for a composition resulting from a particular initial mixture. Whether or not modified by the term "about", the claims include equivalents to the quantities. In one embodiment, the term "about" means within 10% of the reported numerical value, preferably within 5% of the reported numerical value.

In certain embodiments the colour of the preparation may be expressed in terms the ratio between absorbance values at specific wavenumbers. More specifically, in certain embodiments the absorbance at about (circa) 405 nm of a 1% w/v solution of the preparation (based on dry weight) at pH 9 in a 1 cm cell is equal to greater than 500 and the absorbance at about (circa) 653 nm of the same solution is equal to greater than 90 and the ratio of the two absorbance values is about 3.2 to about 5.5

"About (circa) 405 nm" may be taken as 405±3 nm, e.g. 402 to 408 nm, 403 to 407 nm, 404 to 406 nm or 405 nm, or any range which may be derived from these figures. Absorbance at about 405 nm may be greater than about 600, 700, 800, 900, 1000, 1200, 1400, 1600, 1800 or 2000. Absorbance at about 405 nm may about 500 to about 2000, e.g. about 500 to about 1800, 1600, 1400, 1200, 1000, 900, 800, 700, or 600, or about 600, 700, 800, 900, 1000, 1200, 1400, 1600, 1800 to about 2000. Any range which may be formed from any of the above range end points is expressly contemplated.

"About (circa) 653 nm" may be taken as 653±3 nm, e.g. 650 to 656 nm, 651 to 655 nm, 652 to 654 nm or 653 nm, or any range which may be derived from these figures. Absorbance at about 653 nm may be greater than about 100, 120, 140, 160, 180, 200, 220, 240, 260, 280, 300, 320, 340 or 360. Absorbance at about 653 nm may be about 90 to about 360, e.g. about 90 to about 340, 320, 300, 280, 260, 240, 220, 200, 180, 160, 140, 120, or 100, or about 100, 120, 140, 160, 180, 200, 220, 240, 260, 280, 300, 320 or 340 to about 360. Any range which may be formed from any of the above range end points is expressly contemplated.

The ratio of the two absorbance values may be about 3.2 to about 5.4, 5.2, 5.0, 4.8, 4.6, 4.4, 4.2, 4.0, 3.8 or 3.6, or about 3.4, 3.6, 3.8, 4.0, 4.2, 4.4, 4.6, 4.8, 5.0, 5.2, or 5.4 to about 5.5. Any range which may be formed from any of the above range end points is expressly contemplated.

Alternatively expressed, or in addition, in certain embodiments the colour of the preparation may be expressed in terms the hue angle. More specifically, in certain embodiments the hue angle of the preparation will be about 70 to about 175 degrees using HSB/HSL encodings, e.g. about 70 to about 80, 90, 100, 110, 120, 130, 140, 150, 160 or 170, or about 70, 80, 90, 100, 110, 120, 130, 140, 150, 160, or 170 to about 175, or about 70 to about 170, about 80 to about 160, about 90 to about 150, about 100 to about 140, about 110 to about 130, or about 120. Any range which may be formed from any of the above range end points is expressly contemplated.

In nature, chlorophyll may be found in plants, certain algae and cyanobacteria. This pigment is involved in the process of photosynthesis and as such is found typically alongside accessory pigments which may assist in the harvesting of light energy (e.g. phycobiliproteins), filter light to reduce photo-damage and/or act as anti-oxidants (e.g. carotenoids). Chlorophyll containing extracts from such organisms will also contain such accessory pigments and other cellular matter and these compounds require separation from chlorophyll/chlorophyllin in order to prepare a preparation of magnesium chlorophyllin which is suitably pure for industrial use.

In the context of the present invention a preparation of a magnesium chlorophyllin alkali metal salt or alkali earth metal salt is considered substantially, e.g. essentially, pure if, allowing for any solvent present (i.e. liquids in which chlorophyllin is soluble, e.g. water or water miscible organic solvents), the preparation is comprised substantially, e.g. essentially, of a magnesium chlorophyllin alkali metal salt or alkali earth metal salt. If in dry solid form, the preparation will be comprised substantially, e.g. essentially, of a magnesium chlorophyllin alkali metal salt or alkali earth metal salt. Expressed numerically, allowing for any solvent present, the preparation will be comprised of at least 75%, e.g. at least 80%, 85%, 90%, 95%, 96%, 97%, 98%, 99% or 100%, magnesium chlorophyllin alkali metal salt or alkali earth metal salt. Expressed alternatively, allowing for any solvent present, the preparation will be comprised of no more than 25%, e.g. no more than 20%, 15%, 10%, 5%, 4%, 3%, 2%, 1% or 0%, of compounds which are not magnesium chlorophyllin alkali metal salts or alkali earth metal salts. More specifically the content of non-chlorophyllin pigment in the composition will be no more than 25%, e.g. no more than 20%, 15%, 10%, 5%, 4%, 3%, 2%, 1% or 0%. In this context particular mention may be made of chlorophyll, the carotenoids (i.e. the carotenes (e.g. α carotene and/or β carotene) and the xanthophylls (e.g. lutein and/or zeaxanthin)), and the phycobiliproteins (e.g. phycoerythrin, allophycocyanin).

The content of magnesium chlorophyllin alkali metal salt or alkali earth metal salt and/or any impurities which are present may be measured by any convenient analytical means, e.g. HPLC. More conveniently the content of magnesium chlorophyllin alkali metal salt or alkali earth metal salt may be determined by reference to the EU criteria of E140ii provided in EU 231/2012, i.e. a 100% pure sample of chlorophyllin should have at least:

$$E^{1\%}_{1\,cm}$$

700 at ca. 405 nm in aqueous solution at pH 9

$$E^{1\%}_{1\,cm}$$

140 at ca. 653 nm in aqueous solution at pH 9

Preferably, the ratio of said absorbances is 3.2-4.0.

More specifically the content of copper chlorophyllin pigment in the composition will be no more than 25%, e.g. no more than 20%, 15%, 10%, 5%, 4%, 3%, 2%, 1% or 0%. The presence or absence of copper chlorophyllin may be confirmed and quantified by analysing the bathochromic shift which occurs upon mild acidification of an alkaline (e.g. pH 9) solution comprising the preparation of the invention, e.g. acidification to about 6.5 to about 6.9. Magnesium chlorophyllin has a Soret wavelength of 653 nm±5 nm and upon exposure to acid the coordinated $Mg^{2+}$ ion is lost. The resulting chlorophyllin has a Soret wavelength of 667 nm±5 nm. Copper chlorophyllin has a Soret wavelength of 630 nm±5 nm but is not sensitive to acid hydrolysis. In these circumstances the absorbance of an acid treated preparation of chlorophyllin at 630 nm will be caused only by copper chlorophyllin and so will reflect the amount of copper chlorophyllin in the untreated preparation. Likewise, the extent of the decrease in absorbance at 653 nm±5 nm and the increase in absorbance at 667 nm±5 nm upon acid treatment represents the amount of magnesium chlorophyllin in the untreated preparation.

The preparations of magnesium chlorophyllin alkali metal salts or alkali earth metal salts of the invention are also, advantageously, colour-stable, by which it is meant that the preparations retain their colour over a prolonged period of time under suitable storage conditions. For a dry preparation colour will preferably be retained, i.e. stay substantially unchanged, for at least about 3 months, e.g. at least about 4, 6, 8, 10 or 12 months, upon storage under cool, dry and dark conditions. For a liquid preparation colour will preferably be retained, i.e. stay substantially unchanged, for at least about 2 months, e.g. at least about 3, 4, 6, 8, 10 or 12 months, upon storage at a pH of at least about 10 and under cool and dark conditions. By "retained" it is meant that the colour of the preparation does not depart from one or more of the parameter ranges set out above over the specified time period. In certain embodiments, said one or more parameters of the preparation may change (independently) by no more than 25%, e.g. no more than 20%, 15%, 10%, 5%, 4%, 3%, 2%, 1% or 0%, over the specified time period. Colour stability may therefore be measured simply by assessing colour and intensity thereof, as described above, over time.

The plant, algal or cyanobacterial source of the magnesium chlorophyll containing extract is limited only insofar as sufficient amount of the target magnesium chlorophyll may be extracted from the material in useable concentrations. In the case of plants and multicellular algae, it will usually be more efficient to use only those parts of the organism which carry the most chlorophyll, e.g. the leaves, fronds, stems and blades. Particular groups of plants which may conveniently be used as sources of magnesium chlorophyll in accordance with the invention include the mosses, the ferns, the palms, the conifers, the ginkgos, the monocots and the dicots. Within such groups, the grasses, legumes, brassicas and deciduous trees may provide abundant and convenient sources. Within the algae, the aquatic (e.g. marine) chlorophytes may conveniently be used as sources of magnesium chlorophyll in accordance with the invention. Within the cyanobacteria, species within the genus *Arthrosporia* (e.g. *Arthrospira platensis* or *Arthrospira maxima*), in particular in the form of the *Spirulina* health supplement, may be used in accordance with the invention.

In preferred embodiments the source of magnesium chlorophyll is an edible (e.g. by human) plant, algae or cyanobacteria, in particular a source selected from culinary plants, grass, lucerne or nettle.

The target magnesium chlorophyll may be water insoluble or water soluble depending on the presence or absence of a phytyl group. Thus, the magnesium chlorophyll may be selected from chlorophyll a, b, d and f and phytyl-containing homologs thereof (water insoluble) or may be selected from any of the chlorophyll c family or homologs thereof which do not carry a phytyl group (water soluble).

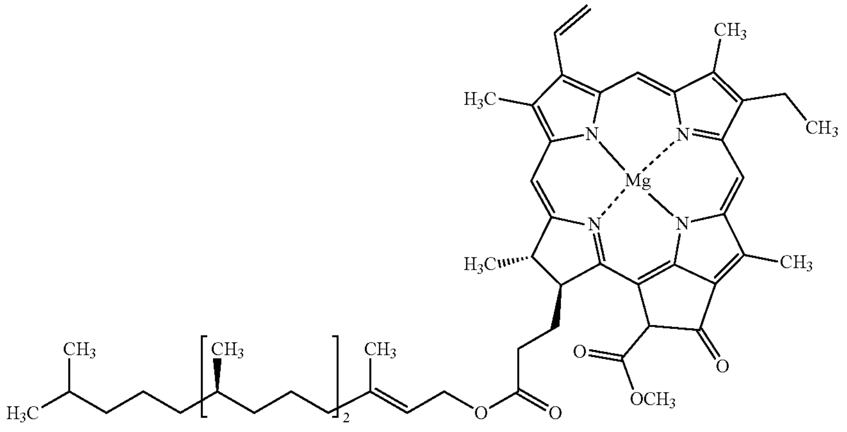

Chlorophyll a

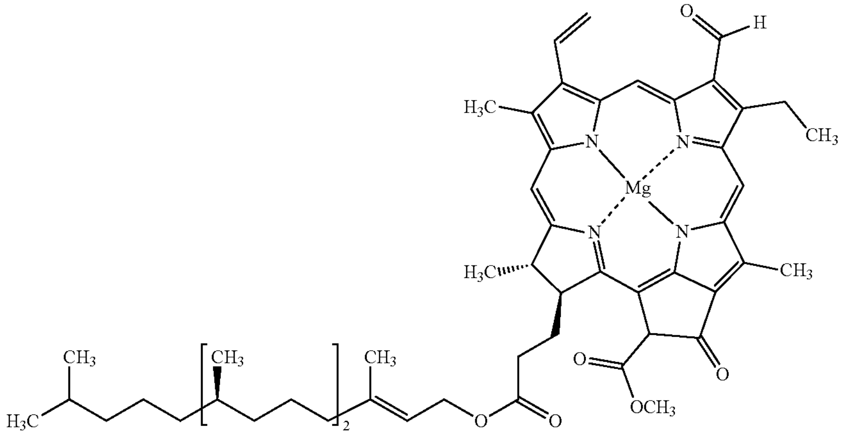

Chlorophyll b

-continued

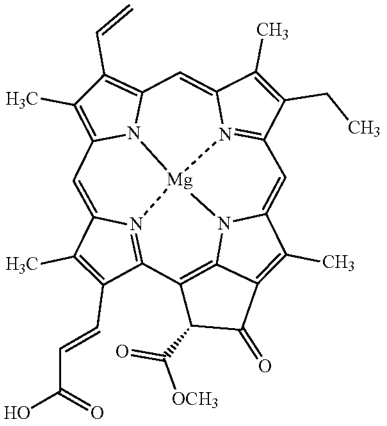

Chlorophyll $c_1$

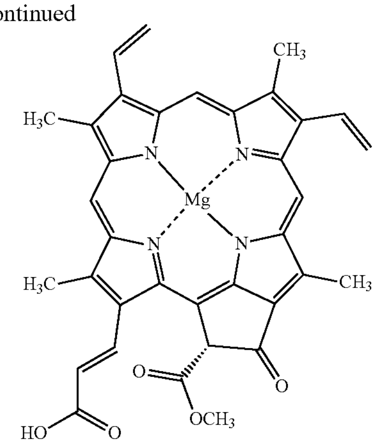

Chlorophyll $c_2$

In embodiments in which the target chlorophyll is water insoluble, the magnesium chlorophyll extract is prepared by treating the natural source material with an organic solvent in which water insoluble chlorophyll is substantially soluble and chlorophyllin is substantially insoluble.

An organic solvent in which water insoluble chlorophyll is substantially soluble can be considered to be an organic compound which is liquid at 20° C. and atmospheric pressure and for which less than about 50 ml is required to solubilise 1 g of chlorophyll at 20° C. and atmospheric pressure. In other embodiments less than about 40, e.g. less than about 30, 20, 10, 9, 8, 7, 6, 5, 4, 3, 2 or 1 ml of the organic compound is required to solubilise 1 g of chlorophyll.

An organic solvent in which chlorophyllin is substantially insoluble can be considered to be an organic compound which is liquid at 20° C. and atmospheric pressure and for which more than about 500 ml is required to solubilise 1 g of chlorophyllin at 20° C. and atmospheric pressure. In other embodiments more than about 600, e.g. more than about 700, 800, 900, 1000, 2000, 5000, or 10,000 ml of the organic compound is required to solubilise 1 g of chlorophyllin.

Such solvents include, but are not limited to, aliphatic ketones having 2 to 8 carbon atoms, branched or unbranched, saturated or unsaturated, in any isomeric form (e.g. acetone, methyl ethyl ketone, diethyl ketone, methyl butyl ketone), aliphatic alcohols having 2 to 8 carbon atoms, branched or unbranched, saturated or unsaturated, in any isomeric form (e.g. pentanol, hexanol, heptanol, octanol), aliphatic ethers having 2 to 8 carbon atoms, branched or unbranched, saturated or unsaturated, in any isomeric form (e.g. diethyl ether, isopropyl ether, dibuytl ether, ethyl hexyl ether, ethyl propyl ether), aliphatic hydrocarbons having 2 to 8 carbon atoms, branched or unbranched, saturated or unsaturated, in any isomeric form (e.g. ethane, propane, butane, pentane, hexane, heptane, octane) halogenated aliphatic hydrocarbons having 2 to 8 carbon atoms, branched or unbranched, saturated or unsaturated, in any isomeric form (e.g. dichloromethane, chloroform), and carbon dioxide. Dichloromethane acetone, methyl ethyl ketone, hexane, or $CO_2$ may be preferred in certain embodiments. Water may also be present in the extracting liquid.

The solubility of chlorophyllin or a water soluble chlorophyll in water (or another substantially, e.g. essentially, aqueous liquid) or the insolubility of a water insoluble chlorophyll in water should be interpreted analogously.

In embodiments in which the target chlorophyll is water soluble, water or other substantially (e.g. essentially) aqueous liquid is used as the primary extracting solvent, although an organic solvent in which chlorophyllin is substantially insoluble may also be present.

In both embodiments an organic solvent in which chlorophyllin is substantially soluble is not present, or at least is present only in nominal amounts which do not affect the yield of the method of the invention. Such solvents include methanol, ethanol, propanol (all isomeric forms), butanol and isopropyl alcohol.

In both embodiments pH should be controlled at equal to or above about pH 7.0 to prevent acid hydrolysis of chlorophyll or chlorophyllin. Reaction parameters including time, temperature and pressure may be dependent on the nature of the source material and the solvents used, e.g. depending on considerations such as volatility and flammability. Following extraction the extract may undergo processing to remove solids and/or solvent.

In certain embodiments, the material undergoing extraction is substantially, e.g. essentially, dry, i.e. is substantially, e.g. essentially, water-free (moisture-free). This may be expressed as a water content of less than 15% w/w, e.g. less than 12, 10, 9%, 8%, 7%, 6%, 5%, 4.5%, 4%, 3.5%, 3%, 2.5%, 2%, 1.5% or 1% w/w as measured by weight loss on drying or chemically by the Karl Fischer method (United States Pharmacopeia; European Pharmacopoeia).

Drying of the source material may be achieved by any convenient means, e.g. air dying, freeze drying, vacuum drying, heating, etc. In certain embodiments, drying occurs immediately following harvesting, e.g. within 24 hours or within 18, 12, 6, 4 or 2 hours. In certain embodiments the source material is combined with a weak alkali (i.e. an alkali which is classified as weakly alkaline and/or a low concentration solution of alkali) prior to or during the drying process to prevent acid hydrolysis of the chlorophyll and loss of colour. In certain embodiments a bicarbonate, e.g. sodium bicarbonate, is applied to the source material. The alkali treated material will have a pH of above about pH 7.0, e.g. up to about pH11.0 prior to drying. The alkaline may be applied as a solution of up to about pH 11.0. The dry source material may be stored in a compressed form, e.g. as pellets, preferably under cool, dry and dark conditions.

The organic solvent which is used to extract water insoluble magnesium chlorophyll from the source material may be water miscible or water immiscible. Should a water miscible solvent be used or if the extracting solvent has been removed, then in certain convenient embodiments the extract may be combined with a water immiscible organic solvent in which chlorophyll is substantially soluble and in which chlorophyllin is substantially insoluble in an amount sufficient to be capable of forming a water immiscible organic phase which may be separable from an aqueous phase.

A water miscible organic solvent is an organic compound which is liquid at 20° C. and atmospheric pressure and which is capable of forming a substantially, e.g. an essentially, homogenous, molecular dispersion with water at any ratio, i.e. is capable of mixing with water in substantially, e.g. essentially, any ratio without separation of two phases.

A water immiscible organic solvent is an organic compound which is liquid at 20° C. and atmospheric pressure and which is incapable of forming a substantially, e.g. an essentially, homogenous, molecular dispersion with water at substantially, e.g. essentially, all ratios, i.e. will form two distinct phases when mixed with water at substantially, e.g. essentially, all ratios.

The liquid composition of step (a)(i) has a oleoresin solids content of about 1% w/v to about 50% w/v, e.g. about 2%, 4%, 6%, 8%, 10%, 12%, 15%, 20%, 25%, 30%, 35%, 40% or 45% w/v to about 50% w/v, or about 1% w/v to about 2%, 4%, 6%, 8%, 10%, 12%, 15%, 20%, 25%, 30%, 35%, 40% or 45% w/v. Any range which may be formed from any of the above range end points is expressly contemplated. The desired oleoresin content may be achieved by diluting the extract with water or an organic solvent, e.g. a water immiscible organic solvent, in which chlorophyllin is substantially insoluble, e.g. those described above, in particular dichloromethane.

The liquid composition of step (a)(i) or step (a)(ii) may have a solids content of about 1% w/v to about 15% w/v, e.g. about 2%, 4%, 6%, 8%, 10%, or 12% w/v to about 15% w/v, or about 1% w/v to about 2%, 4%, 6%, 8%, 10% or 12% w/v. Any range which may be formed from any of the above range end points is expressly contemplated. The desired solids content may be achieved by diluting the extract or liquid component or reconstituting a dried form of the extract or liquid component with water or an organic solvent, e.g. a water immiscible organic solvent, in which chlorophyllin is substantially insoluble, e.g. those described above, in particular dichloromethane.

In certain embodiments, the liquid composition of step (a)(i) is substantially, e.g. essentially, organic, by which is it meant that the composition consists of the chlorophyll containing extract, an organic solvent, e.g. a water immiscible organic solvent, in which chlorophyllin is substantially insoluble (which may be provided as part of the extract) and, if any other components are present, they are predominantly organic molecules. Expressed numerically, less than about 20% v/v, e.g. less than about 10%, 5%, or 1% v/v of the composition of step (a)(i) is water.

In certain embodiments, the liquid composition of step (a)(i) consists of a water immiscible organic phase and an aqueous phase which between them comprise the water insoluble chlorophyll containing extract, a water immiscible organic solvent in which chlorophyllin is substantially insoluble (which may be provided as part of the extract) and water (which may be provided as part of the extract).

In certain embodiments, the liquid composition of step (a)(ii) is substantially, e.g. essentially, aqueous, by which is it meant that the composition consists of the water soluble chlorophyll containing extract, water (which may be provided as part of the extract) and, if any other components are present, they are predominantly inorganic molecules. Expressed numerically, less than about 20% v/v, e.g. less than about 10%, 5%, or 1% v/v of the composition of step (a)(ii) is an organic solvent.

In certain embodiments, the liquid composition of step (a)(ii) consists of a water immiscible organic phase and an aqueous phase which between them comprise the water soluble chlorophyll containing extract, a water immiscible organic solvent in which chlorophyllin is substantially insoluble (which may be provided as part of the extract) and water (which may be provided as part of the extract).

In certain embodiments, the liquid composition of step (a)(iii) consists of a water immiscible organic phase and an aqueous phase which between them comprise the liquid component of plant, cyanobacterial and/or algal matter containing a water-insoluble magnesium chlorophyll, a water immiscible organic solvent in which chlorophyllin is substantially insoluble and water (which may be provided as part of the liquid component).

In step (a), the extract/liquid components may be combined with the other composition components in a dried or semi dried form. In these embodiments the extraction/preparation of the liquid component is performed and then a drying procedure (evaporation, freeze-drying, spray drying) takes place to reduce the content of water and/or organic solvent. The dried/semi dried form is then reconstituted with water and/or organic solvent as necessary.

In certain embodiments step (a)(i) comprises preparing a plant, cyanobacterial and/or algal extract containing a water-insoluble magnesium chlorophyll by treating plant, cyanobacterial and/or algal matter, e.g. substantially dry matter, which contains water insoluble magnesium chlorophyll with an organic solvent in which said chlorophyll is substantially soluble and in which chlorophyllin is substantially insoluble.

The water-insoluble magnesium chlorophyll-containing plant, cyanobacterial and/or algal matter and the treatment thereof may be as described above. In certain embodiments, edible plant matter, grass, lucerne or nettle is treated with dichloromethane, acetone, methyl ethyl ketone, hexane, or $CO_2$.

In certain embodiments step (a)(ii) comprises preparing a plant, cyanobacterial and/or algal extract containing a water-soluble magnesium chlorophyll by treating plant, cyanobacterial and/or algal matter, e.g. substantially dry matter, which contains a water-soluble magnesium chlorophyll with a substantially aqueous liquid in which said chlorophyll is substantially soluble. The water-soluble magnesium chlorophyll-containing plant, cyanobacterial and/or algal matter and the treatment thereof may be as described above.

The liquid component of plant, cyanobacterial and/or algal matter as used in step (a)(iii) is the liquid which may be obtained by performing at least one mechanical means of juice extraction, e.g. by pressing, pulping, mashing, macerating, liquefying and/or sieving, plant, cyanobacterial and/or algal cells and/or tissues, or a concentrated or diluted form of said liquid. The method by which the liquid component may be obtained may also comprise enzyme treatments which breakdown biopolymers. Thus, in certain embodiments step (a)(iii) comprises preparing a liquid component of plant, cyanobacterial and/or algal matter as described above.

A basic inorganic alkali metal salt of use in step (b)(i) of the invention is an inorganic salt of any of lithium (Li), sodium (Na), potassium (K), rubidium (Rb), caesium (Cs), and francium (Fr) which when solubilised in water forms a basic solution. A basic inorganic alkali earth metal salt of use in step (b)(i) of the invention is an inorganic salt of any of beryllium (Be), magnesium (Mg), calcium (Ca), strontium (Sr), barium (Ba), and radium (Ra) which when solubilised in water forms a basic solution. The basic salt used in step (b)(i) in accordance with the invention must be sufficiently basic to maintain a pH of equal to or greater than about 7.0, e.g. greater than 9.5, in the mixture formed in step (b)(i) and as such strong bases may be used. Hydroxides may conveniently be used. Depending on eventual application of the magnesium chlorophyllin alkali metal salt or alkali earth metal salt prepared in accordance with the invention the metal of the salt may be selected accordingly. For instance a radium or francium salt or a salt formed from an isotope of the above listed metals may be selected if a radiolabelled chlorophyllin is desired. For food applications the metal of the salt is preferably selected from lithium, sodium, potassium, calcium or magnesium, although sodium and potassium salts are most preferred, e.g. sodium hydroxide and potassium hydroxide.

The basic salt may be combined with the liquid composition provided in step (a) in solid form before, after or simultaneously with the amount of water to be combined (if any). More conveniently the basic salt may be solubilised in water prior to combination with the substantially organic liquid composition of step (a). The introduction of further solid salt, water or salt solution may still occur during step (b) and also step (c) is not excluded.

An non-nucleophilic organic base of use in step (b)(ii) of the invention may be selected from the tert-butoxides (e.g. $KO^tBu$, $NaO^tBu$, $LiO^tBu$), 1,8-Diazabicyclo(5.4.0)undec-7-ene (DBU), N,N-Diisopropylethylamine (DIPEA), 2,6-Di-tert-butylpyridine, the phosphazene bases (e.g. t-Bu-P4), lithium diisopropylamide, (LDA), the silicon-based amides (e.g. sodium and potassium bis(trimethylsilyl)amide, NaHMDS and KHMDS, respectively), and lithium tetramethylpiperidide (LiTMP).

The base selected may provide sufficient amounts of alkali metal and/or alkali earth metal cations, but if not, additional salts of these metals can be provided. An alkali metal salt of use in step (b)(i) of the invention is a salt of any of lithium (Li), sodium (Na), potassium (K), rubidium (Rb), caesium (Cs), and francium (Fr) and an anionic counter ion, which may be organic or inorganic and which, when solubilised in water, preferably forms a neutral or basic solution. An alkali earth metal salt of use in step (b)(i) of the invention is a salt of any of beryllium (Be), magnesium (Mg), calcium (Ca), strontium (Sr), barium (Ba), radium (Ra) and an anionic counter ion which may be organic or inorganic and which, when solubilised in water, forms a neutral or basic solution. Chloride, fluoride, carbonate or bicarbonate anions may be preferred in these contexts.

Agitation of the mixture formed in step (b)(i) or (b)(ii) and optionally during at least a part of step (c) may be by any convenient means, e.g. stirring, shaking, vortexing, sonication, rotation, rocking and the like.

The amount of base of use in steps (b)(i) and (b)(ii) (e.g. the basic inorganic alkali metal salt and/or a basic inorganic alkali earth metal salt used in step (b)(i) or the non-nucleophilic organic base, ammonia, or a quaternary ammonium salt used in step (b)(ii)) and step (c) if required, is sufficient to maintain a pH of at least about 7.0, e.g. at least about 7.5, 8.0, 8.5, 9.0, 9.5, 10.0, 10.5, 11.0, 11.5, 12.0, 12.5, 13.0, 13.5, 14.0, or 14.5 in the mixture for the duration of steps (b)(i), (b)(ii) and (c) (insofar as step (c) follows steps (b)(i) or b(ii), i.e. until an amount magnesium chlorophyll is converted to a magnesium chlorophyllin alkali metal salt or alkali earth metal salt. In certain embodiments, the reaction is allowed to proceed until substantially, e.g. essentially, all of the magnesium chlorophyll in the mixture is converted to a magnesium chlorophyllin alkali metal salt or alkali earth metal salt.

Expressed numerically, the reaction is allowed to proceed until at least about 80%, e.g. at least about 85%, 90%, 95%, 99% or 100% of the magnesium chlorophyll in the mixture is converted to a magnesium chlorophyllin alkali metal salt or alkali earth metal salt. The progress of this reaction may be monitored by routine means, e.g. monitoring absorbance of the reaction mixture at 405 nm and/or 653 nm, e.g. at a pH adjusted to 7.5 to 9.0. It will be seen therefore that, in certain embodiments, the amount of base and any additional salt used should be in excess of the amount of chlorophyll which is present in the extract.

In these alkaline hydrolysis reaction contexts "conversion" specifically means the alkaline hydrolysis of ester groups in the chlorophyll, in particular the ester group which links the phytyl side chain from the chlorin/porphyrin ring, if present, and the occupation of carboxyl groups with cations of the alkali or alkali earth metal which has been used in the process. In the latter embodiments the reaction is a saponification reaction. The exact structure of the chlorophyllin formed in step (b)(i) and (c) or (b)(ii) and (c) will depend on the structure of the chlorophyll in the starting material, the base (e.g. inorganic alkali metal salt and/or a basic inorganic alkali earth metal salt) used to hydrolyse the ester groups, e.g. the phytyl side chain from the chlorin/porphyrin ring, and the alkali metal salt and/or alkali earth metal salt which may have been used alongside the base. In certain embodiments, the chlorophyllin formed in steps (b)(i) and (c) or (b)(ii) and (c) is a sodium or a potassium salt of magnesium chlorophyllin a or b, e.g. of the formula below, and/or further derivatives formed from the reaction of the side groups present in the chlorophyll with the reagents present and/or the hydrolysis of the cyclic groups, e.g. the cyclopentenyl groups, of the chlorin ring.

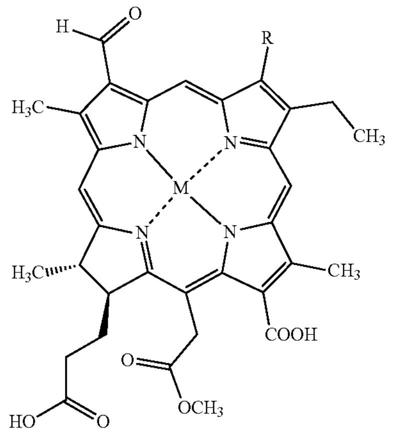

$R = CH_3$ chlorophyllin a
$R = CHO$ chlorophyllin b
M = Mg

The precise conditions sufficient to convert magnesium chlorophyll to a magnesium chlorophyllin alkali metal salt or alkali earth metal salt by alkaline hydrolysis will vary depending on the precise nature of the reaction (e.g. the chemical composition of the extract, the amount of solids in the extract, the strength of the base used and the nature of any accompanying salt used, the temperature of the reaction and the volume of the reaction mixture), but it would be routine for the skilled person to adjust and optimise experimental parameters to ensure efficient de-esterification (e.g. saponification) of the chlorophyll in the reaction. By way of guidance, temperature should be about 0° C. to about 60° C., e.g. about 5° C., 10° C., 15° C., 20° C., 25° C., 30° C., 35° C., 40° C., 45° C., 50° C. or 55° C. to about 60° C. or about 0° C. to about 5° C., 10° C., 15° C., 20° C., 25° C., 30° C., 35° C., 40° C., 45° C., 50° C. or 55° C. Any range which may be formed from any of the above range end points is expressly contemplated. Duration of the reaction may be about 0.5 hrs to about 24 hrs, e.g. about 1, 1.5, 2, 2.5, 3, 3.5, 4, 4.5, 5, 5.5, 6, 9, 12, 15, 18, or 21 hrs to about 24 hrs, or about 0.5 hrs to about 1, 1.5, 2, 2.5, 3, 3.5, 4, 4.5, 5, 5.5, 6, 9, 12, 15, 18, or about 21 hrs. Any range which may be formed from any of the above range end points is expressly contemplated. Multiple additions of the various reagents used may take place and multiple reactions may be pooled.

The chlorophyllase enzyme which may be used in accordance with step (b)(iii) of the invention may be any chlorophyllase capable of hydrolysing an ester group in chlorophyll, in particular the removal of the phytyl group by hydrolysis. The enzyme may be from any convenient source (e.g. plant, algal, bacterial or fungal). In certain embodiments the enzyme will be an enzyme classified as Enzyme Commission class EC 3.1.1.14.

The precise conditions sufficient to convert magnesium chlorophyll to a magnesium chlorophyllin alkali metal salt or alkali earth metal salt by chlorophyllase action will vary depending on the precise nature of the reaction (e.g. the chemical composition of the extract, the amount of solids in the extract, the nature of the enzyme used and the nature of the accompanying salt used, the temperature of the reaction and the volume of the reaction mixture), but it would be routine for the skilled person to adjust and optimise experimental parameters to ensure efficient de-esterification (e.g. saponification) of the chlorophyll in the reaction. By way of guidance, temperature should be about 0° C. to about 40° C., e.g. about 5° C., 10° C., 15° C., 20° C., 25° C., 30° C. or 35° C. to about 40° C. or about 0° C. to about 5° C., 10° C., 15° C., 20° C., 25° C., 30° C. or 35° C. Any range which may be formed from any of the above range end points is expressly contemplated. Duration of the reaction may be about 0.5 hrs to about 24 hrs, e.g. about 1, 1.5, 2, 2.5, 3, 3.5, 4, 4.5, 5, 5.5, 6, 9, 12, 15, 18, or 21 hrs to about 24 hrs, or about 0.5 hrs to about 1, 1.5, 2, 2.5, 3, 3.5, 4, 4.5, 5, 5.5, 6, 9, 12, 15, 18, or about 21 hrs. Any range which may be formed from any of the above range end points is expressly contemplated. Multiple additions of the various reagents used may take place and multiple reactions may be pooled.

Following the de-esterification reaction (e.g. alkaline induced saponification or enzyme catalysed hydrolysis) and salt formation, the magnesium chlorophyllin alkali metal salt or alkali earth metal salt so formed will partition into any aqueous phase of the reaction mixture or will precipitate out of the organic phase.

In accordance with invention an "aqueous phase" of a mixture is a water and hydrophilic molecule containing liquid composition which is immiscible with the non-polar (hydrophobic) organic liquid components of the mixture, which in turn separate into a liquid "water immiscible organic phase". In accordance with the invention the two distinct phases may individually be continuous, but in some instances one may form an emulsion (or similar colloidal suspension) in the other. Either phase may contain solids suspended therein.

Expressed numerically an aqueous phase comprises a solvent portion consisting substantially, e.g. predominantly or essentially, of water, e.g. at least about 80%, 90%, 95%, 99% or 100% of the solvent portion of the entity is water. In other embodiments less than about 20%, 10%, 5%, or 1% of the solvent portion is a non-polar solvent, or at least the amount of non-polar solvent is insufficient to prevent the formation of two distinct phases in the mixture. Solvents with a dielectric constant of less than 15 are generally considered to be non-polar. Expressed differently an aqueous phase can be considered to comprise less than about 20%, 10%, 5%, or 1% of non-polar organic molecules, or at least an amount of non-polar organic molecules that is insufficient to prevent the formation of two distinct phases in the mixture.

Expressed numerically a water immiscible organic phase comprises a solvent portion consisting substantially, e.g. predominantly or essentially, of non-polar (water immiscible) organic molecules, e.g. at least about 80%, 90%, 95%, 99% or 100% of the solvent portion of the entity consists of non-polar (water immiscible) organic molecules. In other embodiments less than about 20%, 10%, 5%, or 1% of the solvent portion is water, or at least the amount of water is insufficient to prevent the formation of two distinct phases in the mixture. Expressed differently, a water immiscible organic phase can be considered to comprise less than about 20%, 10%, 5%, or 1% of water, or at least an amount of water that is insufficient to prevent the formation of two distinct phases in the mixture.

In accordance with the invention the separation of an aqueous phase and a water immiscible organic phase may involve any convenient technique to achieve such separation. This may, for instance, be by allowing the two phases to coalesce into two distinct volumes in a container and then one or other of the phases is drawn away, e.g. by tapping off the denser phase (e.g. with a separation funnel), by pouring off the less dense phase, or by remove a phase by suction (e.g. pipette). If the two phases are present as a colloidal suspension of one or the other the colloidal particles may be separated from the surrounding liquid by filtration or centrifugation or allowing the suspension to settle in a container followed by one or more of the techniques described above for continuous phases. In certain embodiments inorganic, non-alkali salts (e.g. NaCl, KCl, $CaCl_2$) may be added to accelerate interfacial separation.

In accordance with the invention "separation" of an aqueous and an organic phase will result in a substantially, e.g. essentially, none of one phase remaining in the other. Expressed numerically, following separation less than about 20%, 10%, 5%, or 1% of one phase is present in the other, or at least an amount of one phase that is insufficient to prevent the processing of the other in accordance with the invention.

Separation of any precipitated chlorophyllin salt from any organic liquid phase in step (d)(ii) may involve any convenient technique to achieve such separation. The precipitated solids may be removed from the liquid or vice versa. Thus, separation in this context may, for instance, be by filtration using a filter of suitable pore size or by allowing the solids to settle at the base of a container containing the liquid phase under gravity and/or centrifugation and then one or other of the solid or liquid is drawn away, e.g. by tapping or pouring off the liquid, or by removing the solid or liquid by suction (e.g. pipette). In accordance with the invention "separation" of the magnesium chlorophyllin precipitate from the liquid organic phase of step (d)(ii) will result in substantially, e.g. essentially, all magnesium chlorophyllin precipitate being removed from the organic phase. Expressed numerically, following separation less than about 20%, 10%, 5%, or 1% of the precipitated magnesium chlorophyllin will remain in the organic phase, or more that about 80%, 90%, 95%, or 99% of the precipitated magnesium chlorophyllin will be isolated from the liquid organic phase.

The aqueous phase obtained in step (d)(i) following separation from the water immiscible organic phase, or the aqueous phase prepared in step (d)(ii) following the dissolution of the magnesium chlorophyllin precipitate in a substantially aqueous liquid, next undergoes further purification and, if necessary, pH reduction to about 7.0 to about 11.5, e.g. about 7.0 to about 11.0, 10.5, 10.0, 9.5, 9.0, 8.5, 8.0 or 7.5 or about 7.5, 8.0, 8.5, 9.0, 9.5, 10.0, 10.5, or 11.0 to about 11.5. Any range which may be formed from any of the above range end points is expressly contemplated. The use of this range of pH is designed to limit the water solubility of any oil soluble (poorly water soluble, substantially water insoluble) molecules, e.g. certain chlorophyll salts, fatty acids and salts thereof, which promotes their partitioning into the water immiscible organic phase.

These goals are achieved without introducing an acid to the process, which can degrade chlorophyllin metal complexes and alter the colour of the preparation, by combining a water immiscible aliphatic glycerol ester with the aqueous phase obtained in step (d)(i) and/or d(ii). The ester groups in the aliphatic glycerol ester are hydrolysed by hydroxide ions in the reaction mixture, reducing the concentration thereof and thus the pH of the mixture. The aliphatic compounds released by the reaction precipitate out of the reaction mixture or form a water immiscible organic phase. The glycerine released may be removed later, if necessary, by washing the chlorophyllin preparation with acetone or another organic solvent in which glycerine is soluble but chlorophyllin salts are not. If a water immiscible organic solvent in which chlorophyllin is substantially insoluble is also combined at this stage this will contribute to this water immiscible organic phase. As these organic components partition into a water immiscible organic phase, non-polar (hydrophobic) organic impurities in the aqueous phase will partition with them thus cleaning the aqueous phase.

The water immiscible aliphatic glycerol ester may be a mono, di or triglyceride. The aliphatic carbon side chains may individually comprise any number carbon atoms and any number of unsaturated or saturated carbon to carbon bonds so long as the resulting glyceride is water immiscible and is liquid at 20° C. and atmospheric pressure. Thus, the aliphatic side chains may be $C_{4-30}$, e.g. $C_{6-30}$, $C_{8-30}$, $C_{10-30}$, $C_{12-30}$, $C_{14-30}$, $C_{16-30}$, $C_{18-30}$, $C_{20-30}$, $C_{22-30}$, $C_{24-30}$, $C_{26-30}$, $C_{28-30}$, $C_{4-6}$, $C_{4-8}$, $C_{4-10}$, $C_{4-12}$, $C_{4-14}$, $C_{4-16}$, $C_{4-18}$, $C_{4-20}$, $C_{4-22}$, $C_{4-24}$, $C_{4-26}$ or $C_{4-28}$. Any range which may be formed from any of the above range end points is expressly contemplated.

Any reaction between aliphatic glycerol ester and hydroxide is allowed to proceed under agitation at least until a pH of 7.0-11.0 is achieved and/or sufficient extraction of organic impurities has taken place. This may be for about 0.5 hrs to about 24 hrs, e.g. about 1, 1.5, 2, 2.5, 3, 3.5, 4, 4.5, 5, 5.5, 6, 9, 12, 15, 18, or 21 hrs to about 24 hrs, or about 0.5 hrs to about 1, 1.5, 2, 2.5, 3, 3.5, 4, 4.5, 5, 5.5, 6, 9, 12, 15, 18, or about 21 hrs. Any range which may be formed from any of the above range end points is expressly contemplated.

Once the reaction between aliphatic glycerol ester and hydroxide has been allowed to proceed for the desired time the mixture is then incubated for a time and under conditions sufficient to partition substantially water insoluble components into the water immiscible organic phase. This may be for about 0.5 hrs to about 24 hrs, e.g. about 1, 1.5, 2, 2.5, 3, 3.5, 4, 4.5, 5, 5.5, 6, 9, 12, 15, 18, or 21 hrs to about 24 hrs, or about 0.5 hrs to about 1, 1.5, 2, 2.5, 3, 3.5, 4, 4.5, 5, 5.5, 6, 9, 12, 15, 18, or about 21 hrs. Any range which may be formed from any of the above range end points is expressly contemplated. The aqueous phase of the mixture is then separated from the water immiscible organic phase, e.g. as described above.

The aqueous phase obtained in step (g) following separation from the water immiscible organic phase is subsequently combined with a water miscible organic solvent, e.g. an alcohol, in which chlorophyllin is substantially soluble and the mixture is agitated for a time sufficient to substantially solubilise chlorophyllin in the aqueous alcohol phase of the mixture. The solubilisation of chlorophyllin may be monitored by measuring absorbance of the reaction mixture at 405 nm and/or 653 nm, e.g. at a pH adjusted to 7.5 to 9.0. Suitable water miscible alcohols in which chlorophyllin is substantially soluble include methanol, ethanol, propanol (all isomeric forms), isopropyl alcohol.

Once a sufficient degree of chlorophyllin solubilisation has taken place a portion of any solids in the aqueous phase are separated from the aqueous phase. Such solids may comprise residual fatty acids and/or salts thereof. This may involve any convenient technique to achieve such separation. The solids may be removed from the liquid or vice versa. Thus, separation in this context may, for instance, be by filtration using a filter of suitable pore size or by allowing the solids to settle at the base of a container containing the aqueous phase under gravity and/or centrifugation and then one or other of the solid or liquid is drawn away, e.g. by tapping or pouring off the liquid, or by removing the solid or liquid by suction (e.g. pipette). In accordance with the invention "separation" of solids from the aqueous phase of step (j) will result in a substantially, e.g. essentially, no solids remaining in the aqueous phase. Expressed numerically, following separation the aqueous phase will contain less than about 20%, 10%, 5%, or 1%, or at least an amount of solids that is insufficient to prevent the further processing of the aqueous phase in accordance with the invention.

In certain embodiments the aqueous solution of magnesium chlorophyllin alkali metal salt or alkali earth metal salt remaining following separation of solids therefrom may be substantially pure in the sense that the solution consists essentially of magnesium chlorophyllin alkali metal salt or alkali earth metal salt and solvent (i.e., water and water miscible organic solvent, e.g. as defined above). This preparation of magnesium chlorophyllin alkali metal salt or alkali earth metal salt may be used in certain applications, e.g. as described below, without further manipulation or formulation. In other embodiments in may be advantageous to remove some or all of the water miscible organic solvent and/or water from the preparation, for example to provide a more concentrated preparation or a solid (e.g. dry) form of the magnesium chlorophyllin alkali metal salt or alkali earth metal salt.

Removal of the water miscible organic solvent may be by any convenient technique for removing a water miscible organic solvent from an aqueous solution, e.g. by distillation, evaporation, dialysis or chromatographic approaches.

Removal of water from an aqueous solution may be by any convenient technique for removing a water from an aqueous solution, e.g. by distillation, evaporation, dialysis or chromatographic approaches.

In certain embodiments the magnesium chlorophyllin alkali metal salt or alkali earth metal salt preparation of the invention is in the form of a substantially, e.g. essentially, pure and substantially, e.g. essentially, dry solid (e.g. powder). Thus, the dry solid may have a water content of less than 10% w/w, e.g. less than 9%, 8%, 7%, 6%, 5%, 4.5%, 4%, 3.5%, 3%, 2.5%, 2%, 1.5% or 1% w/w as measured by weight loss on drying or chemically by the Karl Fischer method (United States Pharmacopeia; European Pharmacopoeia) and contain at least 75%, e.g. at least 80%, 85%, 90%, 95%, 96%, 97%, 98%, 99% or 100% w/w magnesium chlorophyllin alkali metal salt or alkali earth metal salt, consistent with the definition of purity provided above.

In another aspect the invention provides a colour-stable preparation of a magnesium chlorophyllin alkali metal salt or alkali earth metal salt obtained or obtainable by the methods described herein.

The above described features of the method of the invention are particularly suited to embodiments in which the source material is plant matter (e.g. edible plant material, grass, lucerne or nettle) the chlorophyll extracted therefrom is chlorophyll a and/or b, and the base used is an alkali metal salt (e.g. sodium hydroxide and/or potassium hydroxide). Thus, the magnesium chlorophyllin prepared in such embodiments is the sodium and/or potassium salt of magnesium chlorophyllin. The preparation may be at least 95% pure as defined above and have an absorbance profile and/or hue as defined above. In preferred embodiments the organic solvents used in the process are selected from acetone, methyl ethyl ketone, dichloromethane, carbon dioxide, methanol, ethanol, propan-2-ol and hexane as appropriate. Thus, in preferred embodiments the preparation meets the requirements of the food additive E140(ii) in accordance with EU 231/2012.

As a further aspect the invention further provides a colour stable pigment composition comprising as dry weight at least 90% w/w of a magnesium chlorophyllin alkali metal salt or alkali earth metal salt, wherein said composition has an E1% 1 cm at pH9 of at least 630 at 405±3 nm and at least 126 at 653 nm±3 nm and, optionally, the ratio of the two absorbance values is 3.2 to 5.5.

Features relating to purity, colour and colour stability as defined above apply mutatis mutandis to this aspect of the invention.

In particular, absorbance at 405 nm±3 nm may be at least 644 (92% w/w), at least 665 (95% w/w), at least 686 (98% w/w), at least 693 (99% w/w) or 700 (100% w/w). These w/w percentages are based on the calculated absorbance of a 100% pure magnesium chlorophyllin powder. The E1% 1 cm at pH9 of the preparations of the invention may therefore have absorbance of greater than 700, e.g. greater than about 800, 900, 1000, 1200, 1400, 1600, 1800, or 2000, e.g. 700 to about 2000, e.g. about 800 to about 1800, 1600, 1400, 1200, 1000, 900 or 800, or about 800, 900, 1000, 1200, 1400, 1600, 1800 to about 2000. Any range which may be formed from any of the above range end points is expressly contemplated.

In particular, absorbance at 653±3 nm may be at least 129 (92% w/w), at least 133 (95% w/w), at least 138 (98% w/w), at least 139 (99% w/w) or 140 (100% w/w). These w/w percentages are based on the calculated absorbance of a 100% pure magnesium chlorophyllin powder. The E1% 1 cm at pH9 of the preparations of the invention may therefore have absorbance of greater than 140, e.g. greater than 160, 180, 200, 220, 240, 260, 280, 300, 320, 340, or 360, e.g. about 140 to about 340, 320, 300, 280, 260, 240, 220, 200, 180, or 160, or about 160, 180, 200, 220, 240, 260, 280, 300, 320 or 340 to about 360. Any range which may be formed from any of the above range end points is expressly contemplated.

In particular, the ratio of the two absorbance values may be about 3.2 to about 5.4, 5.2, 5.0, 4.8, 4.6, 4.4, 4.2, 4.0, 3.9, 3.8, 3.7, 3.6, 3.5, 3.4 or 3.3, or about 3.3, 3.4, 3.5, 3.6, 3.7, 3.8, 3.9, 4.0, 4.2, 4.4, 4.6, 4.8, 5.0, 5.2, or 5.4 to about 5.5. Any range which may be formed from any of the above range end points is expressly contemplated.

In particular, the hue angle of the pigment composition may be about 70 to about 175 degrees using HSB/HSL encodings, e.g. about 70 to about 80, 90, 100, 110, 120, 130, 140, 150, 160 or 170, or about 70, 80, 90, 100, 110, 120, 130, 140, 150, 160, or 170 to about 175, or about 70 to about 170, about 80 to about 160, about 90 to about 150, about 100 to about 140, about 110 to about 130, or about 120. Any range which may be formed from any of the above range end points is expressly contemplated.

The preparation and pigment composition of the invention have particular industrial application as colouring agents, especially in the food industry, the animal feed industry, the pharmaceutical industry and the cosmetic industry.

The invention therefore provides a colouring agent comprising, e.g. consisting essentially of, the preparation or pigment composition of the invention.

The invention still further provides a food, beverage, animal feed, pharmaceutical or cosmetic comprising a preparation or pigment composition of the invention as defined herein in an amount sufficient to impart colour to the composition. The preparation or pigment composition of the invention may be used in this context at dry weight equivalent concentrations of about 0.001% to about 1% w/w (as appropriate), e.g. about 0.001% to about 0.5%, 0.1%, 0.05%, 0.01% or about 0.005%, or about 0.005%, 0.01%, 0.05%, 0.1% or 0.5% to about 1% w/w or w/v.

The invention also provides a method for colouring a composition, said method comprising incorporating a preparation or pigment composition of the invention as defined herein into the composition in an amount sufficient to impart colour to the composition, e.g. as defined above. The composition may be a food, beverage, animal feed, pharmaceutical or cosmetic composition.

Examples of beverages which can be coloured using colouring agents of the invention include soft drinks, fruit juices, alcoholic beverages and wine coolers. Examples of foodstuffs which can be coloured using colouring agents of the invention include confectionery (e.g. gummies, hard candies, fruit jellies, chewing gums, marshmallows, jams, fruit preps, chocolates, chocolate fillings, cookie fillings), dairy products (e.g. yoghurts, flavoured milk drinks, cheese, desserts) and bakery and snack products (e.g. breads, doughnuts, cakes, cookies, extruded goods (snacks and cereals), fat-based slurries for snacks). The invention also provides for the colouring of (breakfast) cereals, fruit preparations, dry mixes, ice creams and frozen desserts, meat products, pastas, margarines and sauces and liquid seasonings.

The preparation and pigment composition or the invention also have agricultural applications in the combat of microbial (bacterial, fungal and parasitic) contamination of the surfaces of plants, crops, cropped produce, agricultural infrastructure and equipment, animal carcasses and livestock and more generally in the combat of microbes on other industrial surfaces (especially clinical and food supply chain surfaces) and domestic surfaces. More specifically, chlorophyllins may be used in the photosensitisation-based combat of the microbial contamination of surfaces, e.g. in methods for enhancing the inactivation of food pathogens and harmful microbes by photosensitisation. Said photosensitisation method for combating microbial contamination of surfaces generally entails administering a preparation or pigment composition of the invention as defined herein to (contacting a preparation or pigment composition of the invention with) a surface and/or a microbe in association with said surface and irradiating said surface and/or microbe with light.

Surfaces treatable in accordance with this aspect of the invention may be any surface susceptible to microbial contamination and so may be in vivo surfaces of (i.e. in or on) a living human or animal body and inanimate surfaces (non in vivo surfaces (i.e. not of (i.e. in or on) a living human or animal body)).

Said method may therefore comprise administering a preparation or pigment composition of the invention as defined herein to fresh produce (e.g. fruit (strawberries, raspberries, apricots, peaches), harvested cereal, animal carcasses and butchered meat) and illuminating the treated produce with light (e.g. visible light).

In other embodiments said method may therefore comprise administering a preparation or pigment composition of the invention as defined herein to industrial surfaces (especially surfaces in clinical, agricultural and food supply chain contexts) and domestic surfaces.

The preparation or pigment composition of the invention should be administered in an amount effective to combat contamination of the surface by a microbe upon illumination with an effective amount of light of appropriate wavelength.

"Combating contamination" includes both preventative and reactionary measures or treatments and therefore covers the prevention as well as the reduction, limitation, or elimination of contamination.

By "contamination" it is meant the unwanted presence of a microbe (e.g. a microorganism selected from bacterium, fungus, algae or parasite) at a particular site or location. Contamination can be considered to cover colonisation of a location by a microbe, i.e. the establishment of a microbe at a location and the expansion of the numbers of that organism by replication or the recruitment of additional microbes, which may be of the same or of a different type. The colonisation process may involve the formation of a biofilm.

In these methods the preparation or pigment composition of the invention may be administered in combination with a film forming agent in order to enhance the retention of the chlorophyllin at the target site. Suitable film forming agents include but are not limited to, chitosan, alginate, pectin, cellulose, collagen, carrageen, gum arabic, gum karaya, starch and agar. The preparation or pigment composition of the invention may be formulated with such agents or may be applied separately, either before, after or during application of such agents.

The invention therefore provides a photosensitisation-mediated surface disinfectant composition comprising a preparation or pigment composition of the invention and optionally one or more excipients or diluents. The disinfectant composition may further comprise one or more film forming agents, e.g. those described herein.

In a further aspect of the invention, the preparation or pigment composition of the invention as defined herein is administered in combination with a food supplement, e.g. chitosan, to living animals and said animals are illuminated to effect killing of the microbes.

More particularly, the invention still further provides a photosensitisation-based method for reducing ectoparasitic infection in fish. Said method comprising administering a preparation or pigment composition of the invention as defined herein to fish (e.g. carp, rainbow trout, salmon, cod, mackerel and grayling) and subsequently irradiating said fish with light (e.g. simulated solar radiation) thereby killing the parasites.

The preparation or pigment composition of the invention as defined herein is therefore provided for use in such methods and in methods applied in vivo (i.e. to the living human or animal body).

The wavelength of light used for irradiation may be selected to achieve an efficacious effect. Light having wavelengths of between 300-800 nm, for example, the range 400-700 nm have been found to be particularly effective.

Suitable light sources are natural sunlight, lasers, lamps and LED lamps. The energy consumption per unit time of the lamp or laser system should be such that the heating of tissue does not result in damage to the foodstuff or discomfort or damage to the fish. The irradiation will in general be applied at a dose level of 10 to 200 Joules/$cm^2$, for example 20-60 Joules/$cm^2$, e.g. 38 Joules/$cm^2$. The lamp or laser system may therefore be arranged to provide, in operation, a light intensity in the range of 0.5-100 mW/$cm^2$, e.g. in the range of 1-10 mW/$cm^2$.

The preparation and pigment composition of the invention also have particular therapeutic applications, e.g. as an internal and external odour reducing agent, an antimicrobial, a chronic wound healing agent and in the treatment and prevention of cancer.

Thus, in a further aspect the invention provides a chlorophyllin preparation or a pigment composition as defined herein for use in therapy.

More specifically the invention provides a method for reducing odour in or on a subject, said method comprising administering a preparation or pigment composition of the invention as defined herein internally or externally to a subject in need thereof.

The invention still further provides a method for treating a microbial infection in or on a subject, said method comprising administering a preparation or pigment composition of the invention as defined herein to a subject in need thereof.

The invention still further provides a method for promoting the healing of a chronic wound, said method comprising administering a preparation or pigment composition of the invention as defined herein to a chronic wound in or on a subject in need thereof.

The invention still further provides a method for treating or preventing cancer, said method comprising administering a preparation or pigment composition of the invention as defined herein to a subject in need thereof.

"Treatment" when used in relation to the treatment of a medical condition/infection in a subject in accordance with the invention is used broadly herein to include any therapeutic effect, i.e. any beneficial effect on the condition or in relation to the infection. Thus, not only included is eradication or elimination of the infection, or cure of the subject or infection, but also an improvement in the infection or condition of the subject. Thus included for example, is an improvement in any symptom or sign of the infection or condition, or in any clinically accepted indicator of the infection/condition (for example a decrease in wound size or an acceleration of healing time). Treatment thus includes both curative and palliative therapy, e.g. of a pre-existing or diagnosed infection/condition, i.e. a reactionary treatment.

"Prevention" as used herein refers to any prophylactic or preventative effect. It thus includes delaying, limiting, reducing or preventing the condition (which reference includes infection and contamination, as applicable, in the different aspects of the invention) or the onset of the condition, or one or more symptoms or indications thereof, for example relative to the condition or symptom or indication prior to the prophylactic treatment. Prophylaxis thus explicitly includes both absolute prevention of occurrence or development of the condition, or symptom or indication thereof, and any delay in the onset or development of the condition or symptom or indication, or reduction or limitation on the development or progression of the condition or symptom or indication.

In another aspect the invention provides a preparation or pigment composition of the invention as defined herein for use in the above described methods and therapeutic treatments.

In a still further aspect the invention provides the use of a preparation or pigment composition of the invention as defined herein for the manufacture of a medicament for use in the above described methods and therapeutic treatments.

The preparation or pigment composition of the invention may be administered to the subject in any convenient form or by any convenient means in order to provide an effective amount at the target treatment area, e.g. by topical (e.g. by spray, cream or salve), enteral (e.g. oral, buccal, sublingual, rectal), parenteral (e.g. intravenous) or by inhalation (including nasal inhalation). In certain embodiments, the preparation or pigment composition of the invention will be administered topically, by enteral routes or intravenously.

The skilled person will be able to formulate the preparation or pigment composition of the invention of the invention into pharmaceutical compositions that are adapted for these routes of administration according to any of the conventional methods known in the art and widely described in the literature. In certain embodiments the preparation or pigment composition of the invention may be administered as prepared, i.e. without further formulation.

The present invention therefore also provides a pharmaceutical composition, e.g. for use in any of the above-mentioned therapeutic methods or uses comprising a preparation or pigment composition of the invention as defined herein, together with at least one pharmaceutically acceptable carrier, diluent or excipient, preferably in an amount sufficient to provide a therapeutically effective amount at the target treatment area. This composition may also comprise other therapeutic agents for use in such therapeutic contexts.

More specifically, the preparation or pigment composition of the invention may be incorporated, optionally together with other active agents, with one or more conventional carriers, diluents and/or excipients, to produce conventional galenic preparations such as tablets, pills, powders (e.g. inhalable powders, including dry inhalable powders), lozenges, sachets, cachets, elixirs, suspensions, emulsions, solutions, syrups, aerosols (as a solid or in a liquid medium), sprays (e.g. nasal sprays), compositions for use in nebulisers, ointments, creams, salves, topical sprays, soft and hard gelatine capsules, suppositories, pessaries, sterile injectable solutions, sterile packaged powders, and the like. Enteric coated solid or liquid compositions, sterile sprayable and sterile injectable compositions are of particular note.

Examples of suitable carriers, excipients, and diluents are lactose, dextrose, sucrose, sorbitol, mannitol, starches, gum acacia, calcium phosphate, inert alginate polymers, tragacanth, gelatine, calcium silicate, microcrystalline cellulose, polyvinylpyrrolidone, cellulose, water syrup, water, water/ethanol, water/glycol, water/polyethylene, hypertonic salt water, glycol, propylene glycol, methyl cellulose, methylhydroxybenzoates, propyl hydroxybenzoates, talc, magnesium stearate, mineral oil or fatty substances such as hard fat or suitable mixtures thereof. Excipients and diluents of note are mannitol and hypertonic salt water (saline).

The compositions may additionally include lubricating agents, wetting agents, emulsifying agents, suspending agents, preserving agents, sweetening agents, flavouring agents, and the like.

Parenterally administrable forms, e.g. solutions suitable for intravenous delivery, should be sterile and free from physiologically unacceptable agents, and should have low osmolarity to minimize irritation or other adverse effects upon administration and thus solutions should preferably be isotonic or slightly hypertonic, e.g. hypertonic salt water (saline). Suitable vehicles include aqueous vehicles customarily used for administering parenteral solutions such as sterile water for injection, Sodium Chloride Injection, Ringer's Injection, Dextrose Injection, Dextrose and Sodium Chloride Injection, Lactated Ringer's Injection and other solutions such as are described in Remington's Pharmaceutical Sciences, 15th ed., Easton: Mack Publishing Co., pp. 1405-1412 and 1461-1487 (1975) and The National Formulary XIV, 14th ed. Washington: American Pharmaceutical Association (1975)), which is explicitly incorporated by reference herein in its entirety. The solutions can contain preservatives, antimicrobial agents, buffers and antioxidants conventionally used for parenteral solutions, excipients and other additives which are compatible with chlorophyllin and which will not interfere with the manufacture, storage or use of products.

Solid or liquid formulations of the preparation or pigment composition of the invention may be provided with an enteric coating that prevents degradation in the stomach and/or other parts of the upper GI tract but permits degradation in the lower GI tract, e.g. the small intestine. Such coatings are routinely prepared from polymers including fatty acids, waxes, shellac, plastics, and plant fibres. Specific examples thereof include but are not limited to methyl acrylate-methacrylic acid copolymers, methyl methacrylate-methacrylic acid copolymers, cellulose acetate succinate, hydroxypropyl methylcellulose phthalate, hydroxypropyl methylcellulose acetate succinate (hypromellose acetate succinate), polyvinyl acetate phthalate (PVAP), cellulose acetate trimellitate, and sodium alginate polymer.

For topical administration the preparation or pigment composition of the invention can be incorporated into creams, ointments, gels, salves, transdermal patches, sprays, lotions and the like. In photosensitisation embodiments the formulation will be a photosensitisation-mediated antimicrobial composition and may further contain a film forming agent, e.g. those described above. Further topical systems that are envisaged to be suitable are in situ drug delivery systems, for example gels where solid, semi-solid, amorphous or liquid crystalline gel matrices are formed in situ and which may comprise the preparation or pigment composition of the invention. Such matrices can conveniently be designed to control the release of chlorophyllin from the matrix, e.g. release can be delayed and/or sustained over a chosen period of time. Such systems may form gels only upon contact with biological tissues or fluids, e.g. mucosal surfaces. Typically the gels are bioadhesive and/or mucoadhesive. Delivery to any body site that can retain or be adapted to retain the pre-gel composition can be targeted by such a delivery technique. Such systems are described in WO 2005/023176), which is explicitly incorporated by reference herein in its entirety.

The relative content of the preparation or pigment composition of the invention in the pharmaceutical compositions of the invention can vary depending on the dosage required and the dosage regime being followed but will be sufficient to achieve an effective amount at the target treatment area, taking account of variables such as the physical size of the subject to be treated, the nature of the subject's particular ailments, and the location and identity of the target treatment area. The skilled man would know that the amounts of the preparation or pigment composition of the invention can be reduced if a multiple dosing regime is followed or increased to minimise the number of administrations or applications.

A representative topical formulation, e.g. a cream, ointment or salve, which may be used to administer a preparation or pigment composition of the invention to the skin or a wound might contain 1 to 25%, 1 to 20%, 1 to 15%, 1 to 10%, 1 to 9%, 1 to 8%, 1 to 7%, 1 to 6%, 5 to 25%, 5 to 20%, 5 to 15%, 5 to 10%, 5 to 9%, 5 to 8%, 5 to 7%, 5 to 6%, 8 to 25%, 8 to 20%, 8 to 15%, 8 to 10%, 9 to 25%, 9 to 20%, or 9 to 15% w/v of the preparation or pigment composition of the invention, the remainder being comprised of pharmaceutically acceptable excipients, and/or other active agents if being used.

A representative tablet to be used to administer a preparation or pigment composition of the invention to the lower GI tract may contain up to 75%, 70%, 65% or 60%, e.g. 30 to 75%, 35 to 75%, 40 to 75%, 45 to 75%, 50 to 75%, 55 to 75%, 60 to 75%, 65 to 75%, 70 to 75%, 30 to 70%, 30 to 70%, 35 to 70%, 40 to 70%, 45 to 70%, 50 to 70%, 55 to 70%, 60 to 70%, 65 to 70%, 30 to 65%, 35 to 65%, 40 to 60% or, 45 to 55% w/v or w/w of the preparation or pigment composition of the invention, the remainder being comprised of pharmaceutically acceptable excipients and/or other active agents if being used.

An enteric coated tablet may also be effective in administering a preparation or pigment composition of the invention to the lower GI tract. A representative enteric coated tablet may contain up to 75%, 70%, 65% or 60%, e.g. 30 to 75%, 35 to 75%, 40 to 75%, 45 to 75%, 50 to 75%, 55 to 75%, 60 to 75%, 65 to 75%, 70 to 75%, 30 to 70%, 30 to 70%, 35 to 70%, 40 to 70%, 45 to 70%, 50 to 70%, 55 to 70%, 60 to 70%, 65 to 70%, 30 to 65%, 35 to 65%, 40 to 60% or, 45 to 55% w/v or w/w of the preparation or pigment composition of the invention, the remainder being comprised of pharmaceutically acceptable excipients, including the enteric coating (e.g. polymers including fatty acids, waxes, shellac, plastics, and plant fibres) and/or other active agents if being used.

A representative aqueous solution for intravenous delivery will be sterile and may contain 6 to 25%, e.g. 6 to 20%, 6 to 15%, 6 to 10%, 8 to 25%, 8 to 20%, 8 to 15%, 9 to 25%, 9 to 20%, 9 to 15%, 10 to 15%, 10 to 20%, 10 to 25%, 15 to 20%, or 15 to 25% w/v of the preparation or pigment composition of the invention, the remainder being comprised of water and pharmaceutically acceptable excipients and/or other active agents if being used.

A representative photosensitisation-mediated surface disinfectant composition might contain 1 to 25%, 1 to 20%, 1 to 15%, 1 to 10%, 1 to 9%, 1 to 8%, 1 to 7%, 1 to 6%, 5 to 25%, 5 to 20%, 5 to 15%, 5 to 10%, 5 to 9%, 5 to 8%, 5 to 7%, 5 to 6%, 8 to 25%, 8 to 20%, 8 to 15%, 8 to 10%, 9 to 25%, 9 to 20%, or 9 to 15% w/v of the preparation or pigment composition of the invention, the remainder being comprised of excipients or diluents, and/or other functional or active agents (e.g. film forming agents) if being used.

The invention therefore provides a comprising a preparation or pigment composition of the invention and optionally one or more excipients or diluents. The disinfectant composition may further comprise one or more film forming agents, e.g. those described herein.

The above percentages recited in these formulations may also be taken as references to the amount of chlorophyllin in the formulation as provided by the preparation or pigment composition of the invention.

The invention will be further described with reference to the following non-limiting Examples.

EXAMPLES

The present invention is further defined in the following Examples. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions.

General Materials and Methods

Materials

DCM and methanol were obtained from Acros.

Potassium hydroxide (>85%), and Acetone 100% was obtained from VWR

RWD sunflower oil was obtained from Kerfoot

Filtration paper: Whatman No 1

Instruments

UV-Vis Spectroscopy: Perkin Elmer lambda 25

Determination of Absorbance by UV-Vis Spectroscopy:

The absorbance of 1% solutions of chlorophyllin samples (in pH 9 sodium hydrogen phosphate/potassium hydroxide buffer) were measured at 403 nm and 653 nm. Measurements were determined using a 1 cm cell.

Example 1—Preparation of a Potassium Salt of Magnesium Chlorophyllin from a Natural Source (*Medicago sativa*)

Chlorophyll extract, prepared by treating lucerne (*Medicago sativa*) with acetone (25 g, 11.4% chlorophyll in acetone/chloroform), was diluted with DCM to 10% w/w solids. KOH (10 g, 50 wt %) was added and the resulting biphasic reaction mixture vigorously stirred at room temperature for 2 hours. The pH of the solution was 14. The organic layer was removed. DCM (150 g) and sunflower oil (5 g) were added to the aqueous layer and the resulting biphasic mixture was stirred for 1 hour. The organic layer was removed. Methanol (100 g) was added to the aqueous phase and the resulting solution stirred for 1 hour. The reaction mixture was filtered and the filtrate evaluated without drying.

Observations: sample was green when dried and redissolves.

Dry content: 0.6%, 96 g collected

Yield: 27.5%

Purity: 136% in accordance with the criteria of EU 231/2012

Absorbance of a 1% solution of the liquid chlorophyllin preparation @ 403 nm: 5.778. This is calculated as equivalent to an absorbance of 963 @ 403 nm for a 1% solution of the dry powder (5.778×100/0.6).

pH of aqueous methanol solution of chlorophyllin—10.6

Example 2—Preparation of a Potassium Salt of Magnesium Chlorophyllin from a Natural Source (Fescue)

1. An extract of grass (fescue) was prepared by treating dried grass with dichloromethane.

2. The solvent was removed to give a product of 25.14% chlorophyll content.
3. 25 g of this was taken and dissolved at 40 C in acetone then allowed to cool to ambient (18 C).
4. The acetone layer was separated from the solid using a filter.
5. 1.6 g of potassium hydroxide (50% solution) was mixed in to the acetone layer and stirred for 90 mins.
6. The acetone and layer was filtered. A paste was also collected from the mixing flask.
7. Both solids were washed with 50 mL of acetone then 2×10 ml of water. The precipitate dissolving into the water.
8. 180 g of acetone was added mixed and left 20 mins. The precipitate was centrifuged.
9. Finally, the filtrate was diluted into 15 mL of DI water filtered and dried.

Yield was 2.03 g—42%, E1% 1 cm was 921 (purity of 131% according to EU231/2012). pH of a 1% solution—10.7

Example 3—Preparation of a Potassium Salt of Magnesium Chlorophyllin from a Natural Source (Alfalfa)

1. An extract of alfalfa was prepared by treating dried alfalfa with Acetone then hexane.
2. The solvent was removed to give a product of 24% chlorophyll content.
3. 1.4 g of this was taken and dissolved at 40 C in acetone then allowed to cool to ambient (18 C).
4. The acetone layer was separated from the solid using a filter.
5. 0.2 g of potassium hydroxide (50% solution) was mixed in to the acetone layer and stirred for 90 mins.
6. The Acetone layer was decanted post centrifuging 10 mins @ 3600 rcf
7. Solid was washed with 8% water in acetone twice
8. The solid was then washed with 100% acetone at 40 C
9. Solid was dried Yield was 0.1254 g—46%, E1% 1 cm was 854 at 406 nm (purity of 122% according to EU231/2012). pH of a 1% solution—10.0

Illustrative embodiments of the disclosure include:

According to a first illustrative embodiment, discloses is a method for preparing a colour-stable preparation of a magnesium chlorophyllin alkali metal salt or alkali earth metal salt, said method comprising either:

(a)(i) providing a liquid composition comprising a plant, cyanobacterial and/or algal extract containing a water-insoluble magnesium chlorophyll, wherein said extract has been prepared by treating plant, cyanobacterial and/or algal matter containing a water-insoluble magnesium chlorophyll with an organic solvent in which said chlorophyll is substantially soluble and chlorophyllin is substantially insoluble, wherein said composition has a oleoresin solids content of about 1% w/w to about 50% w/w and does not comprise an organic solvent in which chlorophyllin is substantially soluble; or (a)(ii) providing a liquid composition comprising a plant, cyanobacterial and/or algal extract containing a water-soluble magnesium chlorophyll, wherein said extract has been prepared by treating plant, cyanobacterial and/or algal matter containing a water-soluble magnesium chlorophyll with a substantially aqueous liquid in which said chlorophyll is substantially soluble, wherein said composition does not comprise an organic solvent in which chlorophyllin is substantially soluble; or (a)(iii) providing a liquid composition comprising the liquid component of plant, cyanobacterial and/or algal matter containing a water-insoluble magnesium chlorophyll, and an organic solvent in which said chlorophyll is substantially soluble and chlorophyllin is substantially insoluble, wherein said composition does not comprise an organic solvent in which chlorophyllin is substantially soluble; and either (b)(i) combining an amount of a basic inorganic alkali metal salt and/or a basic inorganic alkali earth metal salt, and optionally an amount of water, with an amount of said the liquid composition of step (a)(i), step (a)(ii) or step (a)(iii) and agitating the mixture so formed, wherein the amount of salt, and the amount of water if used, is sufficient to maintain a pH of equal to or greater than about 7.0 in the mixture; or (b)(ii) combining an amount of a non-nucleophilic organic base, ammonia, or a quaternary ammonium salt, and optionally, an alkali metal salt and/or an alkali earth metal salt, and optionally an amount of water, with an amount of said the liquid composition of step (a)(i), step (a)(ii) or step (a)(iii) and agitating the mixture so formed, wherein the amount of base, and the amount of water and salt, if used, is sufficient to maintain a pH of equal to or greater than about 7.0 in the mixture; or (b)(iii) combining an amount of said the liquid composition of step (a)(i), step (a)(ii) or step (a)(iii) with a chlorophyllase and alkali metal salt and/or an alkali earth metal salt, and optionally an amount of water, wherein the mixture so formed has a pH of equal to or greater than about 7.0; and (c) incubating the mixture of step (b)(i), (b)(ii) or (b)(iii) under conditions sufficient to convert magnesium chlorophyll to a magnesium chlorophyllin alkali metal salt or alkali earth metal salt; and either (d)(i) separating at least a portion of any aqueous phase of the mixture of step (c) from any water immiscible organic phase of the mixture of step (c); or (d)(ii) separating at least a portion of any precipitated magnesium chlorophyllin in the mixture of step (c) from any organic phase and redissolving said precipitate in an substantially aqueous liquid to form an aqueous phase; and (e) combining (i) an amount of a water immiscible aliphatic glycerol ester with an amount of the aqueous phase obtained in step (d)(i) and/or (d)(ii) and, optionally, (ii) an amount of a water immiscible organic solvent in which chlorophyll is substantially soluble and chlorophyllin is substantially insoluble, and agitating the mixture so formed, wherein the amount of ester added, and the amount of solvent if added, are sufficient to be capable of forming a water immiscible organic phase which may be separable from the aqueous phase and, if necessary, reduce the pH of the mixture so formed to about 7.0 to about 11.5; and (f) incubating the mixture under conditions sufficient to reduce the pH of the mixture so formed to about 7.0 to about 11.5, if necessary, and/or to partition substantially water insoluble components into the water immiscible organic phase; and (g) separating at least a portion of the aqueous phase of the mixture of step (f) from the water immiscible organic phase of the mixture of step (f); and (h) adding an amount of a water miscible organic solvent in which chlorophyllin is substantially soluble to an amount of the portion of the aqueous phase obtained in step (g) and agitating the mixture so formed, wherein the amount of organic solvent is sufficient to substantially solubilise chlorophyllin in the aqueous phase of the mixture;

(i) incubating the mixture of step (h) under conditions sufficient to substantially solubilise chlorophyllin in the aqueous phase of the mixture of step (h);

(j) separating at least a portion of any solids in the mixture of step (i) from the aqueous phase of said mixture, thereby providing an aqueous solution of said magnesium chlorophyllin alkali metal salt or alkali earth metal salt; and optionally, (k) removing at least a portion of said water miscible organic solvent from the aqueous chlorophyllin solution of step (j); and/or optionally, (l) removing at least a portion of the water present in the aqueous chlorophyllin solution of step (j) or step (k).

According to a second illustrative embodiment, disclosed is the method of the first illustrative embodiment, wherein for the colour-stable preparation of a magnesium chlorophyllin alkali metal salt or alkali earth metal salt, the absorbance at about 405 nm of a 1% w/v solution of the preparation based on dry weight at pH 9 in a 1 cm cell is equal to greater than 500 and the absorbance at about 653 nm of the same solution under the same conditions is equal to greater than 90.

According to a third illustrative embodiment, disclosed is the method of the second illustrative embodiment, wherein The method of claim 2 wherein the absorbance at about 405 nm is greater than about 600.

According to a fourth illustrative embodiment, disclosed is the method of the second illustrative embodiment, wherein absorbance at about 653 nm is greater than about 100.

According to a fifth illustrative embodiment, disclosed is the method of the second illustrative embodiment, wherein the ratio of the absorbance values taken at 405 nm and those taken at 653 nm is about 3.2 to about 5.4.

According to a sixth illustrative embodiment, disclosed is the method of the first illustrative embodiment, wherein the preparation is substantially pure.

According to a seventh illustrative embodiment, disclosed is the method of the first illustrative embodiment, wherein the source of the plant matter is a moss, a fern, a palm, a conifer, a ginkgo, a monocot or a dicot.

According to an eighth illustrative embodiment, disclosed is the method of the first illustrative embodiment, wherein the source of the algal matter is a chlorophyte.

According to a ninth illustrative embodiment, disclosed is the method of the first illustrative embodiment, wherein the source of the cyanobacterial matter is a species within the genus *Arthrosporia.*

According to a tenth illustrative embodiment, disclosed is the method of the first illustrative embodiment, wherein the magnesium chlorophyll is selected from the group consisting of chlorophyll a, b, d and f and phytyl-containing homologs thereof.

According to an eleventh illustrative embodiment, disclosed is the method of the first illustrative embodiment, wherein the magnesium chlorophyll is selected from the group consisting of any of the chlorophyll c family or homologs thereof which do not carry a phytyl group.

According to a twelfth illustrative embodiment, disclosed is the method of the first illustrative embodiment, wherein in step (a)(i) the organic solvent in which water insoluble chlorophyll is substantially soluble and chlorophyllin is substantially insoluble is selected from the group consisting of:

(i) acetone, methyl ethyl ketone, diethyl ketone, methyl butyl ketone (ii) pentanol, hexanol, heptanol, octanol, (iii) diethyl ether, isopropyl ether, dibuytl ether, ethyl hexyl ether, ethyl propyl ether, (iv) ethane, propane, butane, pentane, hexane, heptane, octane (v) dichloromethane, chloroform, and (vi) carbon dioxide.

According to a thirteenth illustrative embodiment, disclosed is the method of the twelfth illustrative embodiment, wherein, in step (a)(i) the organic solvent in which water insoluble chlorophyll is substantially soluble and chlorophyllin is substantially insoluble is selected from the group consisting of dichloromethane, acetone, methyl ethyl ketone, hexane, and $CO_2$.

According to a fourteenth illustrative embodiment, disclosed is the method of the first illustrative embodiment, wherein the basic inorganic alkali metal salt of step (b)(i) is an inorganic salt of any of lithium, sodium, potassium, rubidium, caesium, and francium which when solubilised in water forms a basic solution.

According to a fifteenth illustrative embodiment, disclosed is the method of the first illustrative embodiment, wherein the basic inorganic alkali earth metal salt of step (b)(i) is an inorganic salt of any of beryllium, magnesium, calcium, strontium, barium, and radium which when solubilised in water forms a basic solution.

According to a sixteenth illustrative embodiment, disclosed is the method of the first illustrative embodiment, wherein the basic inorganic salt is sodium hydroxide or potassium hydroxide.

According to a seventeenth illustrative embodiment, disclosed is the method of the first illustrative embodiment, wherein the non-nucleophilic organic base of step (b)(ii) is selected from the group consisting of: the tert-butoxides; 1,8-Diazabicyclo(5.4.0)undec-7-ene (DBU); N,N-Diisopropylethylamine (DIPEA); 2,6-Di-tert-butylpyridine; the phosphazene bases; lithium diisopropylamide (LDA); the silicon-based amides; and lithium tetramethylpiperidide (LiTMP).

According to a eighteenth illustrative embodiment, disclosed is the method of the first illustrative embodiment, wherein the water immiscible aliphatic glycerol ester is selected from the group consisting of mono, di or triglyceride forms of the aliphatic glycerol ester.

According to a nineteenth illustrative embodiment, disclosed is the method of the eighteenth illustrative embodiment, wherein the aliphatic side chain/chains of the water immiscible aliphatic glycerol ester are independently $C_{4-6}$, $C_{4-8}$, $C_{4-10}$, $C_{4-12}$, $C_{4-14}$, $C_{4-16}$, $C_{4-18}$, $C_{4-20}$, $C_{4-22}$, $C_{4-24}$, $C_{4-26}$, $C_{4-28}$, or $C_{4-30}$.

According to a twentieth illustrative embodiment, disclosed is the method of the first illustrative embodiment, wherein in step (g) the water miscible organic solvent is selected from the group consisting of methanol, ethanol, propanol, and isopropyl alcohol.

According to a twenty-first illustrative embodiment, disclosed is a colour-stable preparation of a magnesium chlorophyllin alkali metal salt or alkali earth metal salt obtained or obtainable by the method of the first illustrative embodiment.

According to a twenty-second illustrative embodiment, disclosed is a colour-stable preparation of the twenty-first illustrative embodiment, wherein the preparation is in the form of a substantially dry solid, preferably a powder.

According to a twenty-third illustrative embodiment, disclosed is a colour stable pigment composition comprising as dry weight at least 90% w/w of a magnesium chlorophyllin alkali metal salt or alkali earth metal salt, wherein said composition has an E1% 1 cm at pH9 of at least 630 at 405±3 nm and at least 126 at 653 nm±3 nm and, preferably, the ratio of the two absorbance values is 3.2 to 5.5.

According to a twenty-fourth illustrative embodiment, disclosed is the method of the first illustrative embodiment, wherein:

(i) for a dry preparation or pigment composition, colour is retained for at least about 12 months, upon storage under cool, dry and dark conditions, and (ii) for a liquid preparation or pigment composition, colour is retained for at least about 12 months, upon storage at a pH of at least about 10 and under cool and dark conditions.

According to a twenty-fifth illustrative embodiment, disclosed is the colour stable pigment composition of the twenty-third illustrative embodiment, wherein absorbance at 405 nm±3 nm is at least 644.

According to a twenty-sixth illustrative embodiment, disclosed is the colour stable pigment composition of the twenty-third illustrative embodiment, wherein absorbance at 653±3 nm is at least 129.

According to a twenty-seventh illustrative embodiment, disclosed is the colour stable pigment composition of the twenty-third illustrative embodiment, wherein the ratio of the two absorbance values is about 3.2 to about 5.5.

According to a twenty-eighth illustrative embodiment, disclosed is the colour stable pigment composition of the twenty-third illustrative embodiment, wherein the hue angle of the composition may be about 70 to about 175.

According to a twenty-ninth illustrative embodiment, disclosed is a colouring agent comprising the preparation of the twenty-first illustrative embodiment.

According to a thirtieth illustrative embodiment, disclosed is a colouring agent comprising the pigment composition of the twenty-third illustrative embodiment.

According to a thirty-first illustrative embodiment, disclosed is a food, beverage, animal feed, pharmaceutical or cosmetic comprising the preparation of the twenty-first illustrative embodiment, as a colouring agent in an amount sufficient to impart a green colour to the composition or part thereof.

According to a thirty-second illustrative embodiment, disclosed is a food, beverage, animal feed, pharmaceutical or cosmetic comprising the pigment composition of the twenty-third illustrative embodiment, as a colouring agent in an amount sufficient to impart a green colour to the composition or part thereof.

The invention claimed is:

1. A colour stable and water soluble pigment composition comprising as dry weight at least 90% w/w of a magnesium chlorophyllin alkali metal salt or alkali earth metal salt, wherein said composition has an E1% 1 cm at pH 9 of at least 630 at 405±3 nm and at least 126 at 653 nm±3 nm, wherein an absorbance ratio of the E1% 1 cm value at 405±3 nm to the E1% 1 cm value at 653 nm±3 nm is in the range about 3.2 to about 5.5, wherein colour stable is defined as the absorbance ratio changing by no more than about 25% after at least about 2 months of storage, for a liquid preparation or liquid pigment composition, or at least about 3 months of storage, for a dry preparation or dry pigment composition.

2. The colour stable pigment composition of claim 1, wherein absorbance at 405 nm±3 nm is at least 644.

3. The colour stable pigment composition of claim 1, where absorbance at 653±3 nm is at least 129.

4. The colour stable pigment composition of claim 1, wherein the hue angle of the composition is about 70 to about 175.

5. A colouring agent comprising the colour stable pigment composition of claim 1.

6. A food, beverage, animal feed, pharmaceutical or cosmetic comprising the colour stable pigment composition of claim 1 as a colouring agent in an amount sufficient to impart a green colour to the food, beverage, animal feed, pharmaceutical or cosmetic or part thereof.

7. The colour stable preparation of a magnesium chlorophyllin alkali metal salt, according to claim 1, prepared by the method comprising:

(a) providing a liquid composition comprising a plant extract containing a water-insoluble magnesium chlorophyll, wherein said extract has been prepared by treating plant matter containing a water-insoluble magnesium chlorophyll with an organic solvent in which said chlorophyll is substantially soluble and chlorophyllin is substantially insoluble, wherein said composition has an oleoresin solids content of about 1% w/w to about 50% w/w and does not comprise an organic solvent in which chlorophyllin is substantially soluble;

(b) combining an amount of a basic inorganic alkali metal salt with an amount of the liquid composition of step (a) and agitating the mixture so formed, wherein the amount of salt is sufficient to maintain a pH of equal to or greater than about 7.0 in the mixture;

(c) incubating the mixture of step (b) under conditions sufficient to convert magnesium chlorophyll to a magnesium chlorophyllin alkali metal salt;

(d) separating at least a portion of a first aqueous phase of the mixture of step (c) from a first water immiscible organic phase of the mixture of step (c);

(e) combining an amount of water immiscible aliphatic glycerol ester with an amount of the first aqueous phase obtained in step (d) wherein the amount of ester added is sufficient to be capable of forming a second water immiscible organic phase which is separable from the first aqueous phase;

(f) separating at least a portion of the first aqueous phase of the mixture of step (e) from the second water immiscible organic phase of the mixture of step (e);

(g) adding an amount of a water miscible organic solvent in which chlorophyllin is substantially soluble to an amount of the portion of the first aqueous phase obtained in step (f) and agitating the mixture so formed, wherein the amount of organic solvent is sufficient to substantially solubilize chlorophyllin in the first aqueous phase of the mixture;

(h) incubating the mixture of step (g) under conditions sufficient to substantially solubilize chlorophyllin in the first aqueous phase of the mixture of step (g); and (i) separating at least a portion of any solids in the mixture of step (h) from the first aqueous phase of said mixture, thereby providing an aqueous solution of said magnesium chlorophyllin alkali metal salt.

8. The colour stable preparation of a magnesium chlorophyllin alkali metal salt of claim 7, wherein step (d) alternatively comprises separating at least a portion of any precipitated magnesium chlorophyllin in the mixture of step (c) from any organic phase and redissolving said precipitate in an a substantially aqueous liquid to form a second aqueous phase.

9. The colour stable preparation of magnesium chlorophyllin alkali metal salt of claim 8, further comprising step (e)(2) incubating the mixture of step (e) under conditions sufficient to reduce the pH of the mixture so formed to about 7.0 to about 11.5.

10. The colour stable preparation of magnesium chlorophyllin alkali metal salt of claim 7, further comprising step (j) removing at least a portion of said water miscible organic solvent from the aqueous chlorophyllin solution of step (i).

11. The colour stable preparation of magnesium chlorophyllin alkali metal salt of claim 10, further comprising step (k) removing at least a portion of the water present in the aqueous chlorophyllin solution of step (i) or step (j).

12. The colour stable preparation of magnesium chlorophyllin alkali metal salt of claim 7, wherein the source of the plant matter is a moss, a fern, a palm, a conifer, a ginkgo, a monocot or a dicot.

13. The colour stable preparation of magnesium chlorophyllin alkali metal salt of claim 7, wherein the magnesium chlorophyll is selected from the group consisting of chlorophyll a, b, d, and f and phytyl-containing homologs thereof.

14. The colour stable preparation of magnesium chlorophyllin alkali metal salt of claim 7, wherein the magnesium chlorophyll is selected from the group consisting of any of the chlorophyll c family or homologs thereof which do not carry a phytyl group.

15. The colour stable preparation of magnesium chlorophyllin alkali metal salt of claim 7, wherein in step (a) the organic solvent in which water insoluble chlorophyll is substantially soluble and chlorophyllin is substantially insoluble is selected from the group consisting of: acetone, methyl ethyl ketone, methyl butyl ketone, pentanol, hexanol, heptanol, octanol, diethyl ether, isopropyl ether, dibutyl ether, ethyl hexyl ether, ethyl propyl ether, ethane, propane, butane, pentane, hexane, heptane, octane, dichloromethane, chloroform, and carbon dioxide.

16. The colour stable preparation of magnesium chlorophyllin alkali metal salt of claim 15, wherein, in step (a) the organic solvent in which water insoluble chlorophyll is substantially soluble and chlorophyllin is substantially insoluble is selected from the group consisting of dichloromethane, acetone, methyl ethyl ketone, hexane, and $CO_2$.

17. The colour stable preparation of magnesium chlorophyllin alkali metal salt of claim 7, wherein the basic inorganic alkali metal salt of step (b) is an inorganic salt of any of lithium, sodium, potassium, rubidium, caesium, and francium which when solubilised in water forms a basic solution.

18. The colour stable preparation of magnesium chlorophyllin alkali metal salt of claim 7, wherein the basic inorganic salt is sodium hydroxide or potassium hydroxide.

19. The colour stable preparation of magnesium chlorophyllin alkali metal salt of claim 7, wherein the water immiscible aliphatic glycerol ester is selected from the group consisting of mono, di or triglyceride forms of the aliphatic glycerol ester.

20. The colour stable preparation of magnesium chlorophyllin alkali metal salt of claim 19, wherein the aliphatic side chain/chains of the water immiscible aliphatic glycerol ester are independently $C_{4-6}$, $C_{4-8}$, $C_{4-10}$, $C_{4-12}$, $C_{4-14}$, $C_{4-16}$, $C_{4-18}$, $C_{4-20}$, $C_{4-22}$, $C_{4-26}$, $C_{4-28}$ or $C_{4-30}$.

21. The colour stable preparation of magnesium chlorophyllin alkali metal salt of claim 9, wherein in step (g) the water miscible organic solvent is selected from the group consisting of methanol, ethanol, propanol, and isopropyl alcohol.

22. The colour stable preparation of a magnesium chlorophyllin alkali metal salt of claim 11, wherein the amount of water miscible organic solvent removed in step (j) and the amount of water removed in step (k) is sufficient to yield the preparation in the form of a substantially dry solid.

23. The colour stable preparation of magnesium chlorophyllin alkali metal salt of claim 7, wherein: (i) for a dry preparation or dry pigment composition, colour stability is retained for at least about 12 months, upon storage under cool, dry and dark conditions, and (ii) for a liquid preparation or liquid pigment composition, colour stability is retained for at least about 12 months, upon storage at a pH of at least about 10 and under cool and dark conditions.

24. The colour stable preparation of magnesium chlorophyllin alkali metal salt of claim 7, wherein the colour-stable preparation of a magnesium chlorophyllin alkali metal salt or alkali earth metal salt, the absorbance at about 405 nm of a 1% w/v solution of the preparation based on dry weight at pH 9 in a 1 cm cell is equal to or greater than 500 and the absorbance at about 653 nm of the same solution under the same conditions is equal to greater than 90.

25. The colour stable preparation of magnesium chlorophyllin alkali metal salt of claim 7, wherein the preparation is substantially pure.

26. A colouring agent comprising the colour stable preparation of magnesium chlorophyllin alkali metal salt according to claim 7.

27. A food, beverage, animal feed, pharmaceutical or cosmetic comprising the colour stable preparation of magnesium chlorophyllin alkali metal salt according to claim 7 as a colouring agent in an amount sufficient to impart a green colour to the food, beverage, animal feed, pharmaceutical or cosmetic or part thereof.

* * * * *